US008550344B2

(12) United States Patent
Jung et al.

(10) Patent No.: US 8,550,344 B2
(45) Date of Patent: *Oct. 8, 2013

(54) SPECIALTY STENTS WITH FLOW CONTROL FEATURES OR THE LIKE

(75) Inventors: Edward K. Y. Jung, Bellevue, WA (US); Robert Langer, Newton, MA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1138 days.

This patent is subject to a terminal disclaimer.

(21) Appl. No.: 11/454,343

(22) Filed: Jun. 16, 2006

(65) Prior Publication Data

US 2009/0084844 A1 Apr. 2, 2009

(51) Int. Cl.
*G06F 19/00* (2011.01)

(52) U.S. Cl.
USPC ............. 235/385; 235/375; 235/380; 705/28; 705/64; 705/65

(58) Field of Classification Search
USPC ............ 235/375, 380, 385; 705/3, 28, 64, 65; 623/1.11, 1.15, 1.16, 1.45
See application file for complete search history.

(56) References Cited

U.S. PATENT DOCUMENTS

| | | |
|---|---|---|
| 4,575,805 A | 3/1986 | Moermann et al. |
| 5,407,431 A | 4/1995 | Botich et al. |
| 5,733,868 A | 3/1998 | Peterson et al. |
| 5,823,948 A | 10/1998 | Ross, Jr. et al. |
| 5,954,701 A | 9/1999 | Matalon |
| 5,966,693 A | 10/1999 | Burgess |
| 5,966,963 A | 10/1999 | Kovalaske |
| 6,112,109 A | 8/2000 | D'Urso |
| 6,120,502 A | 9/2000 | Michelson |
| 6,149,433 A | 11/2000 | Ziegler et al. |
| 6,184,030 B1 | 2/2001 | Katoot et al. |
| 6,231,514 B1 | 5/2001 | Lowe et al. |
| 6,458,153 B1 | 10/2002 | Bailey et al. |
| 6,464,687 B1 | 10/2002 | Ishikawa et al. |
| 6,481,262 B2 | 11/2002 | Ching et al. |
| 6,532,964 B2 | 3/2003 | Aboul-Hosn et al. |

(Continued)

OTHER PUBLICATIONS

Rothenberg, et al.; "'Sleeve' Keeps Blockages at Bay"; USA Today Magazine; bearing a date of Feb. 1998; pp. 1-2; vol. 126, Issue 2633.

(Continued)

*Primary Examiner* — Michael G Lee
*Assistant Examiner* — Tabitha Chedekel

(57) ABSTRACT

Methods and systems are described for obtaining a parameter relating to a stent inventory shortage or to a specific patient and for configuring a stent in response. For example, the response may involve configuring a stent with a flow occlusion portion in response to the obtained parameter relating to the stent inventory shortage, configuring a stent with a flow occlusion portion in response to receiving the parameter relating to the specific patient, or specializing one or more stents in response to obtaining the parameter relating to the stent inventory shortage.

48 Claims, 22 Drawing Sheets

(56) References Cited

U.S. PATENT DOCUMENTS

| | | | |
|---|---|---|---|
| 6,569,104 B2 | 5/2003 | Ono et al. | |
| 6,592,565 B2 | 7/2003 | Twardowski | |
| 6,592,605 B2 | 7/2003 | Lenker et al. | |
| 6,663,765 B2 | 12/2003 | Cherkes | |
| 6,685,738 B2 | 2/2004 | Chouinard et al. | |
| 6,702,847 B2 | 3/2004 | DiCarlo | |
| 6,726,696 B1 | 4/2004 | Houser et al. | |
| 6,726,923 B2 | 4/2004 | Iyer et al. | |
| 6,730,252 B1 | 5/2004 | Teoh et al. | |
| 6,754,357 B2 | 6/2004 | McIntosh et al. | |
| 6,793,668 B1 | 9/2004 | Fisher | |
| 6,918,929 B2 | 7/2005 | Udipi et al. | |
| 6,951,053 B2 * | 10/2005 | Padilla et al. | 29/557 |
| 6,972,031 B1 | 12/2005 | Braginsky et al. | |
| 6,996,245 B2 | 2/2006 | Hanna | |
| 7,326,240 B1 | 2/2008 | Caro et al. | |
| 7,371,067 B2 | 5/2008 | Anderson et al. | |
| 7,583,367 B2 | 9/2009 | Ikeda et al. | |
| 7,698,068 B2 | 4/2010 | Babayoff | |
| 7,804,991 B2 | 9/2010 | Abovitz et al. | |
| 7,818,084 B2 | 10/2010 | Boyden et al. | |
| 8,095,382 B2 | 1/2012 | Boyden et al. | |
| 8,147,537 B2 | 4/2012 | Boyden et al. | |
| 8,163,003 B2 | 4/2012 | Boyden et al. | |
| 8,224,632 B2 | 7/2012 | Whirley et al. | |
| 8,252,039 B2 | 8/2012 | Golesworthy et al. | |
| 2001/0025131 A1 | 9/2001 | Edwin et al. | |
| 2001/0039504 A1 * | 11/2001 | Linberg et al. | 705/3 |
| 2001/0056357 A1 | 12/2001 | Irving et al. | |
| 2002/0006401 A1 | 1/2002 | Rogers et al. | |
| 2002/0023843 A1 | 2/2002 | Cherkes | |
| 2002/0035555 A1 | 3/2002 | Wheeler et al. | |
| 2002/0068968 A1 | 6/2002 | Hupp | |
| 2002/0137014 A1 * | 9/2002 | Anderson et al. | 434/262 |
| 2002/0183628 A1 | 12/2002 | Reich et al. | |
| 2002/0198587 A1 | 12/2002 | Greenberg et al. | |
| 2003/0018294 A1 * | 1/2003 | Cox | 604/20 |
| 2003/0047126 A1 | 3/2003 | Tomaschko | |
| 2003/0060782 A1 | 3/2003 | Bose et al. | |
| 2003/0149335 A1 | 8/2003 | Silverman et al. | |
| 2003/0200120 A1 | 10/2003 | Binkert | |
| 2004/0024443 A1 | 2/2004 | Dwyer et al. | |
| 2004/0117005 A1 | 6/2004 | Nagarada Gadde et al. | |
| 2004/0149294 A1 | 8/2004 | Gianchandani et al. | |
| 2004/0204751 A1 | 10/2004 | Fischell et al. | |
| 2004/0230131 A1 | 11/2004 | Kassab et al. | |
| 2005/0037133 A1 | 2/2005 | Halleriet et al. | |
| 2005/0038342 A1 | 2/2005 | Mozayeni et al. | |
| 2005/0049691 A1 | 3/2005 | Mericle et al. | |
| 2005/0061336 A1 | 3/2005 | Goetz et al. | |
| 2005/0096498 A1 | 5/2005 | Houser et al. | |
| 2005/0107817 A1 | 5/2005 | White et al. | |
| 2005/0107867 A1 | 5/2005 | Taheri | |
| 2005/0177223 A1 | 8/2005 | Palmaz | |
| 2005/0203457 A1 | 9/2005 | Smego | |
| 2005/0251183 A1 | 11/2005 | Buckman et al. | |
| 2005/0267569 A1 | 12/2005 | Barrett et al. | |
| 2005/0273157 A1 | 12/2005 | Pinchasik | |
| 2005/0288763 A1 | 12/2005 | Andreas et al. | |
| 2006/0058638 A1 | 3/2006 | Boese et al. | |
| 2006/0079740 A1 | 4/2006 | Silver et al. | |
| 2006/0122697 A1 | 6/2006 | Shanley et al. | |
| 2006/0129228 A1 | 6/2006 | Golesworthy et al. | |
| 2006/0149348 A1 | 7/2006 | Vogel et al. | |
| 2006/0178551 A1 | 8/2006 | Melvin | |
| 2006/0206038 A1 * | 9/2006 | Jenkins et al. | 600/587 |
| 2006/0280351 A1 | 12/2006 | Luping et al. | |
| 2007/0021816 A1 | 1/2007 | Rudin | |
| 2007/0083258 A1 | 4/2007 | Falotico et al. | |
| 2007/0112581 A1 | 5/2007 | Smith et al. | |
| 2007/0118243 A1 | 5/2007 | Schroeder et al. | |
| 2007/0148626 A1 | 6/2007 | Ikeda | |
| 2007/0168066 A1 | 7/2007 | Grishaber et al. | |
| 2008/0015677 A1 | 1/2008 | Glossop et al. | |
| 2008/0030497 A1 | 2/2008 | Hu et al. | |
| 2008/0121046 A1 | 5/2008 | Glezer et al. | |
| 2008/0234831 A1 | 9/2008 | Clarke et al. | |
| 2008/0243284 A1 | 10/2008 | Grishaber et al. | |
| 2009/0099652 A1 | 4/2009 | Granada et al. | |

OTHER PUBLICATIONS

UK Intellectual Property Office Examination Report under section 18(3); Application No. GB1001635.0; Feb. 1, 2012 (Received by our Agent 3 Feb. 3, 2012); pp. 1-2.
UK Intellectual Property Office Examination Report under section 18(3); Application No. GB1001639.2; Feb. 1, 2012 (Received by our Agent Feb. 3, 2012); pp. 1-2.
PCT International Search Report; International App. No. PCT/US2008/008813; Jan. 9, 2009; pp. 1-2.
Bertolero, Art; Ibrahim, Tamer; Geyster, Steve; "Ventricular Restoration"; pp. 1-10
"Intellectual Property"; Patent Disclosure Form; bearing a date of Sep. 2, 2003; pp. 1-9; Case #CHFT-MRI-01.
"Press Release: SurModics Provides Hydrophilic Coating on Xtent's Drug-Eluting Stent Delivery System"; Business Wire: Financial News; bearing a date of May 15, 2006; pp. 1-2; Yahoo! Inc.
"Tracking Acute Myocardial Infarction: The First Step in Treating Ischemic CHF"; CHFT Proposal; bearing a date of 1999; pp. 1-4; American College of Cardiology and American Heart Association, Inc.
Twardowski, Z.J.; Haynie, J.D.; "Measurements of Hemodialysis Catheter Blood Flow in Vivo"; The International Journal of Artificial Organs; bearing a date of 2002; pp. 276-280; vol. 25, No. 4; Wichtig Editore.
Twardowski, Z.J.; Seger, R.M.; "Dimensions of Central Venous Structures in Humans Measured in Vivo Using Magnetic Resonance Imaging: Implications for Central-Vein Catheter Dimensions"; The International Journal of Artificial Organs; bearing a date of 2002; pp. 107-123; vol. 25, No. 2; Wichtig Editore.
Van Der Giessen, Willem J., PhD., MD; Van Beusekom, Heleen M.M.; Larsson, Rolf; Serruys, Patrick W., PhD., MD; "Heparin-Coated Coronary Stents"; Current Interventional Cardiology Reports; bearing a date of 1999; pp. 234-240; vol. 1; Current Science Inc.
"Xtent Custom I Trial Shows Zero Restenosis, Favorable Late Loss Results at Eight Months"; Healthcare Sales & Marketing Network NewsFeed; bearing a date of May 16, 2006; pp. 1-2.
"Xtent Customized Stent System Achieves Two Coronary Firsts: Single Catheter Delivers Multiple Stents and Longest Stent Ever Placed"; News & Information About Minimally Invasive Medicine; bearing dates of 1996-2006 and Jan. 5, 2006; pp. 1-2; Venture Digital LLC.
U.S. Appl. No. 13/135,437, Jung et al.
PCT International Search Report; International App. No. PCT/US07/14260; Jul. 30, 2008; pp. 1-4.
PCT International Search Report; International App. No. PCT/US07/14025; Aug. 8, 2008; pp. 1-4.
PCT International Search Report; International App. No. PCT/US07/14267; Aug. 14, 2008; pp. 1-2.
U.S. Appl. No. 12/804,897, Edward K.Y. Jung et al.
U.S. Appl. No. 11/455,010, Jung et al.
U.S. Appl. No. 11/526,089, Jung et al.
U.S. Appl. No. 11/526,203, Jung et al.
U.S. Appl. No. 11/526,144, Jung et al.
U.S. Appl. No. 11/526,201, Jung et al.
U.S. Appl. No. 11/541,492, Jung et al.
U.S. Appl. No. 11/541,452, Jung et al.
U.S. Appl. No. 11/541,378, Jung et al.
U.S. Appl. No. 11/541,377, Jung et al.
U.S. Appl. No. 11/541,448, Jung et al.
U.S. Appl. No. 13/135,726, Jung et al.
U.S. Appl. No. 13/134,999, Jung et al.

* cited by examiner

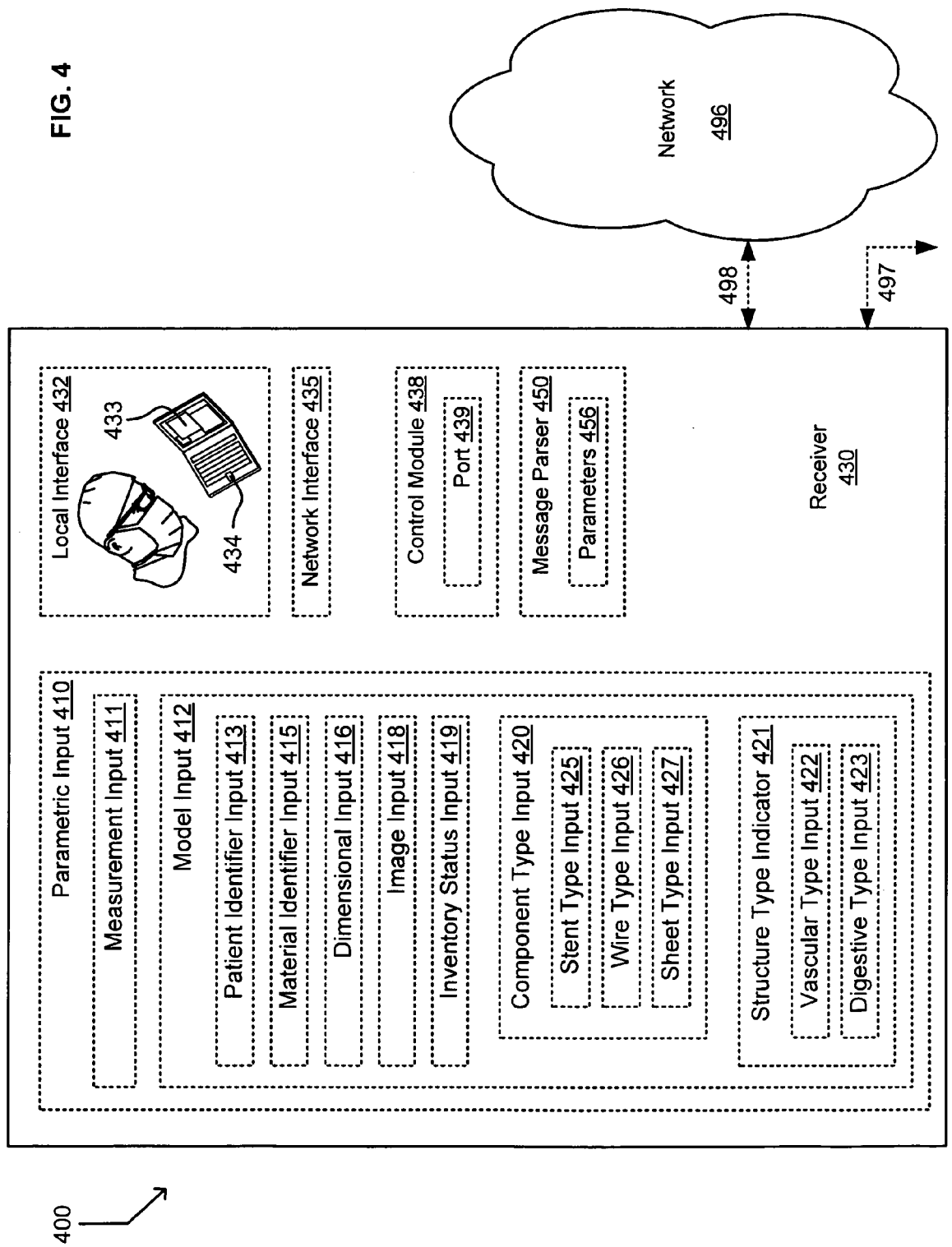

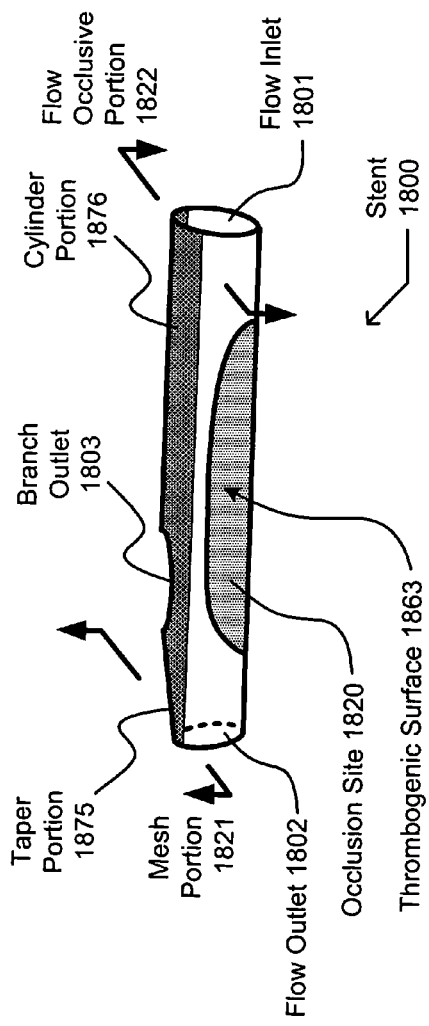
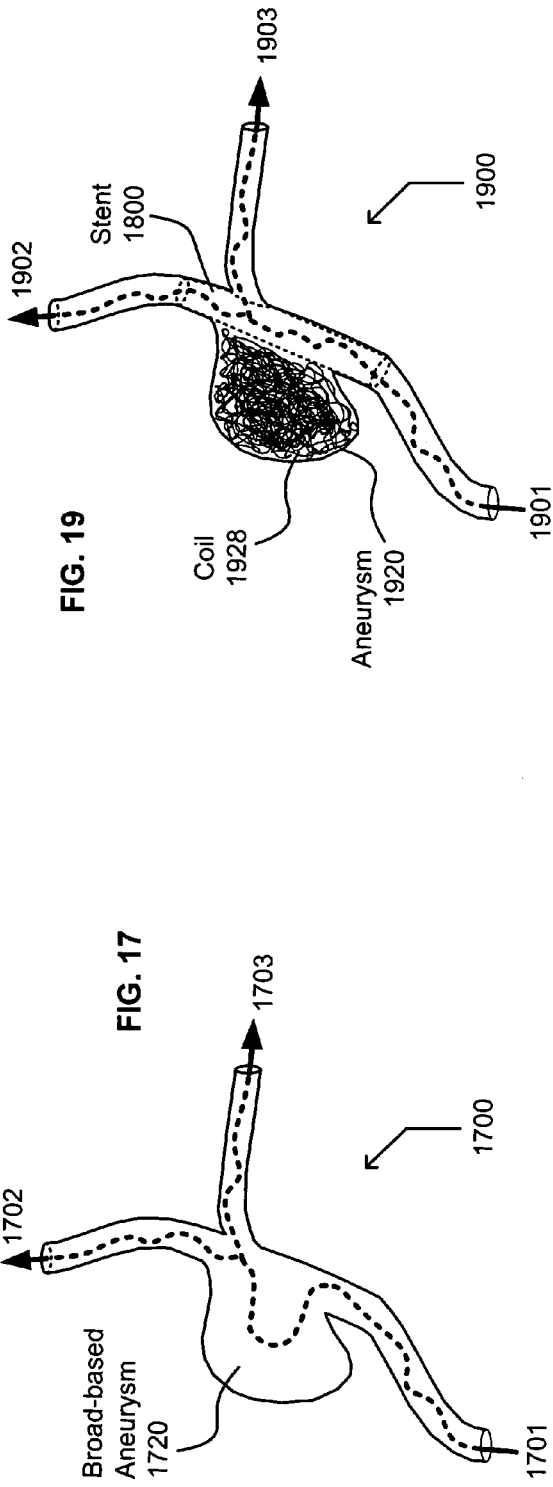

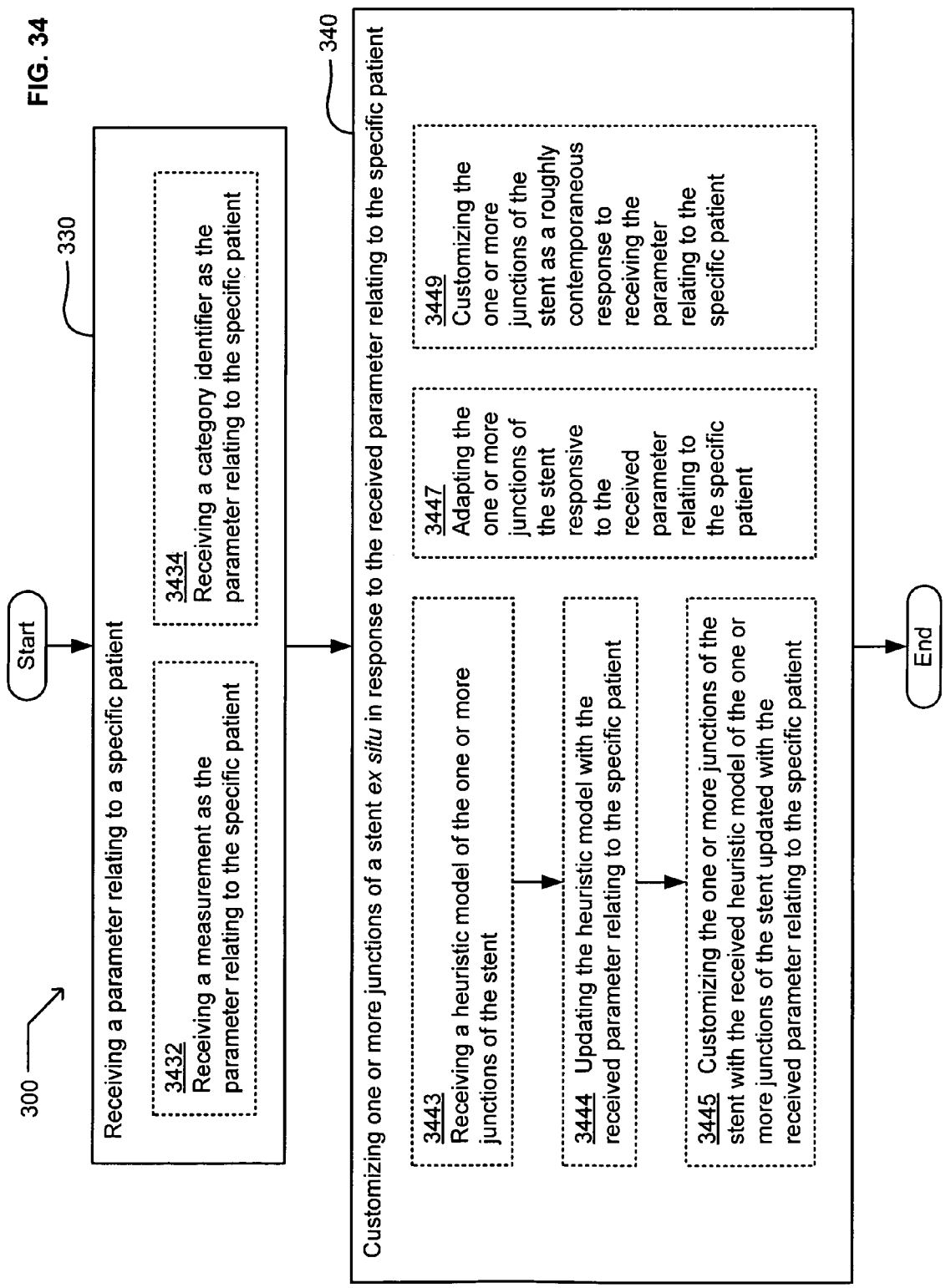

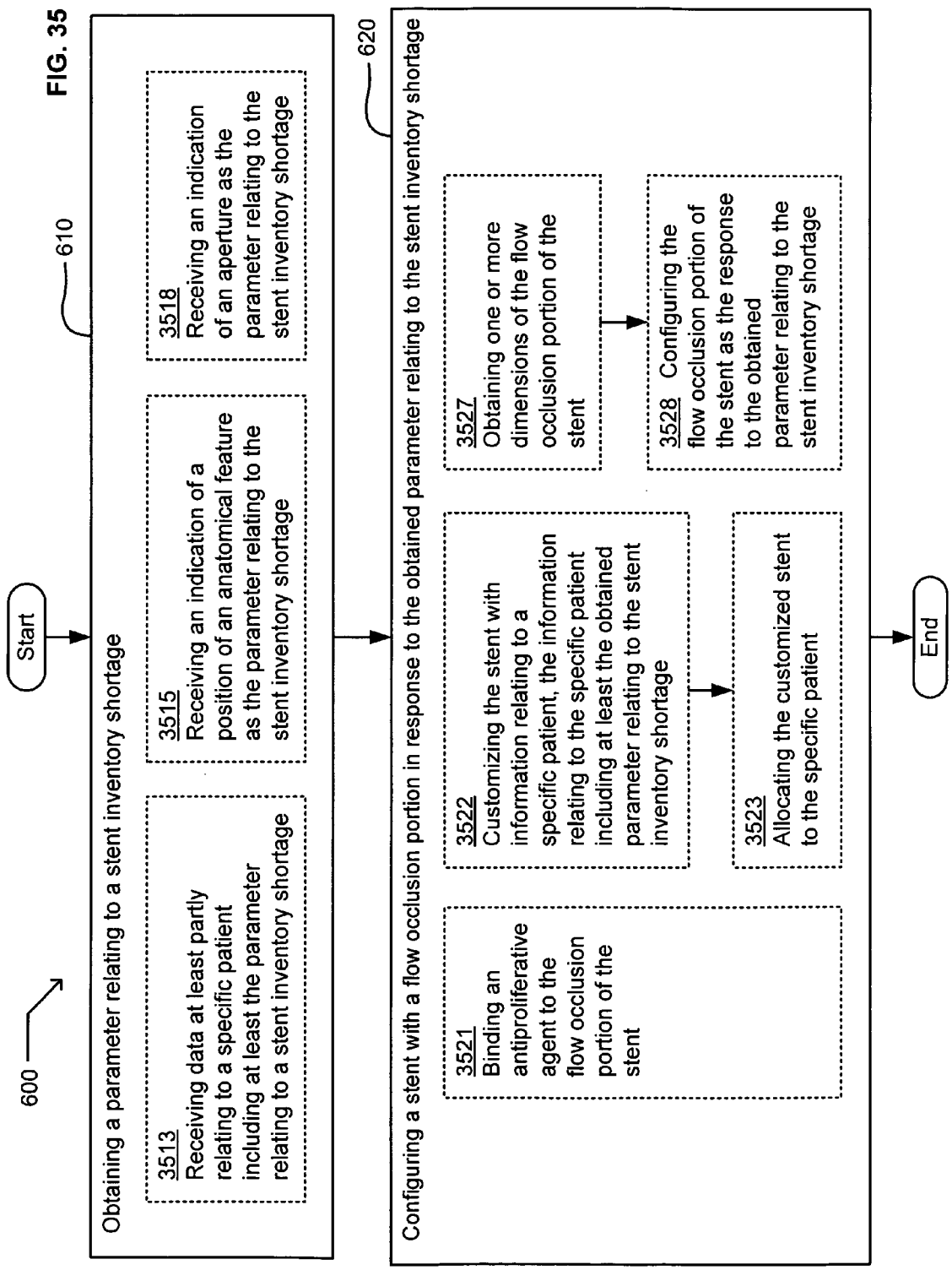

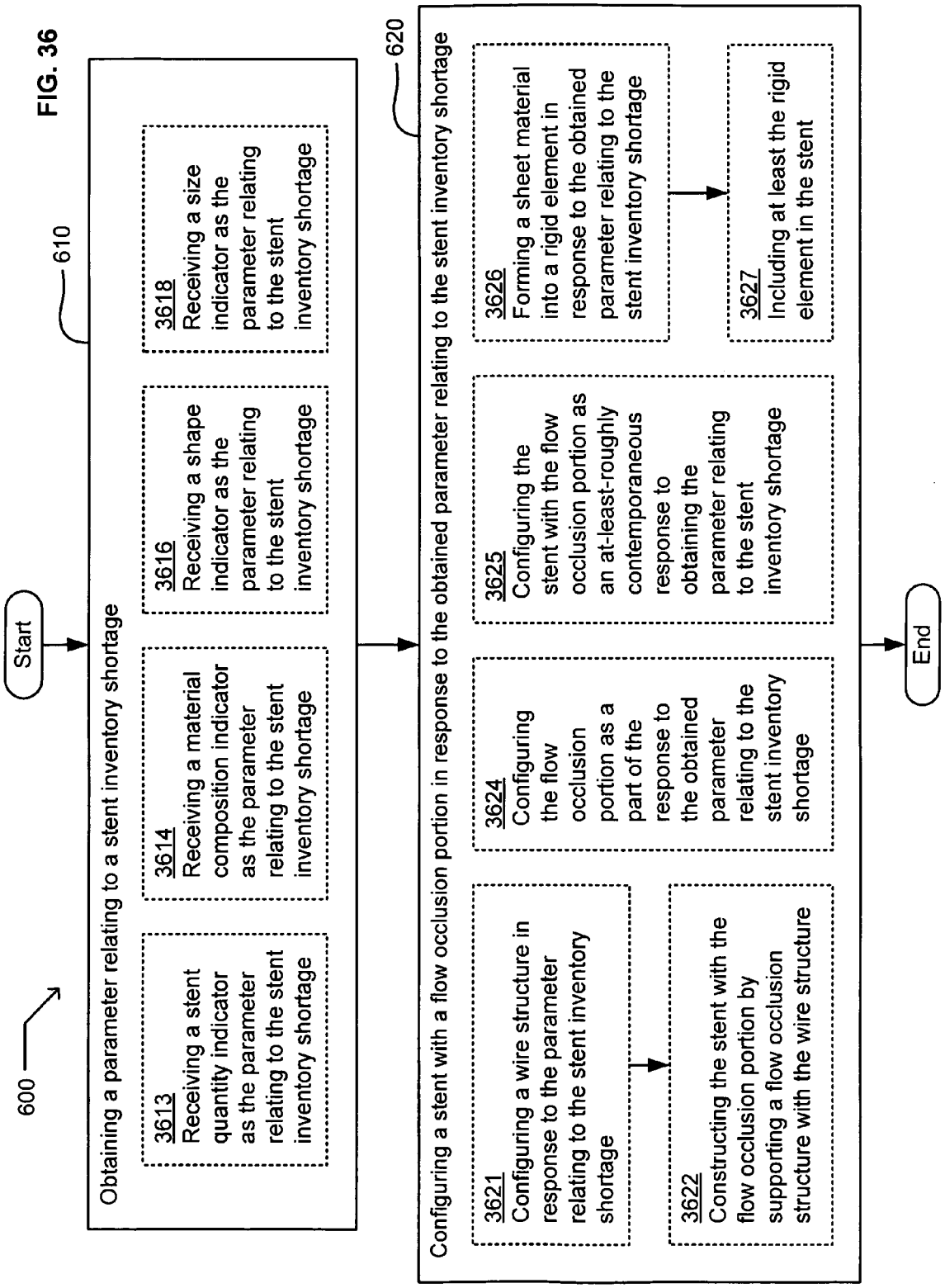

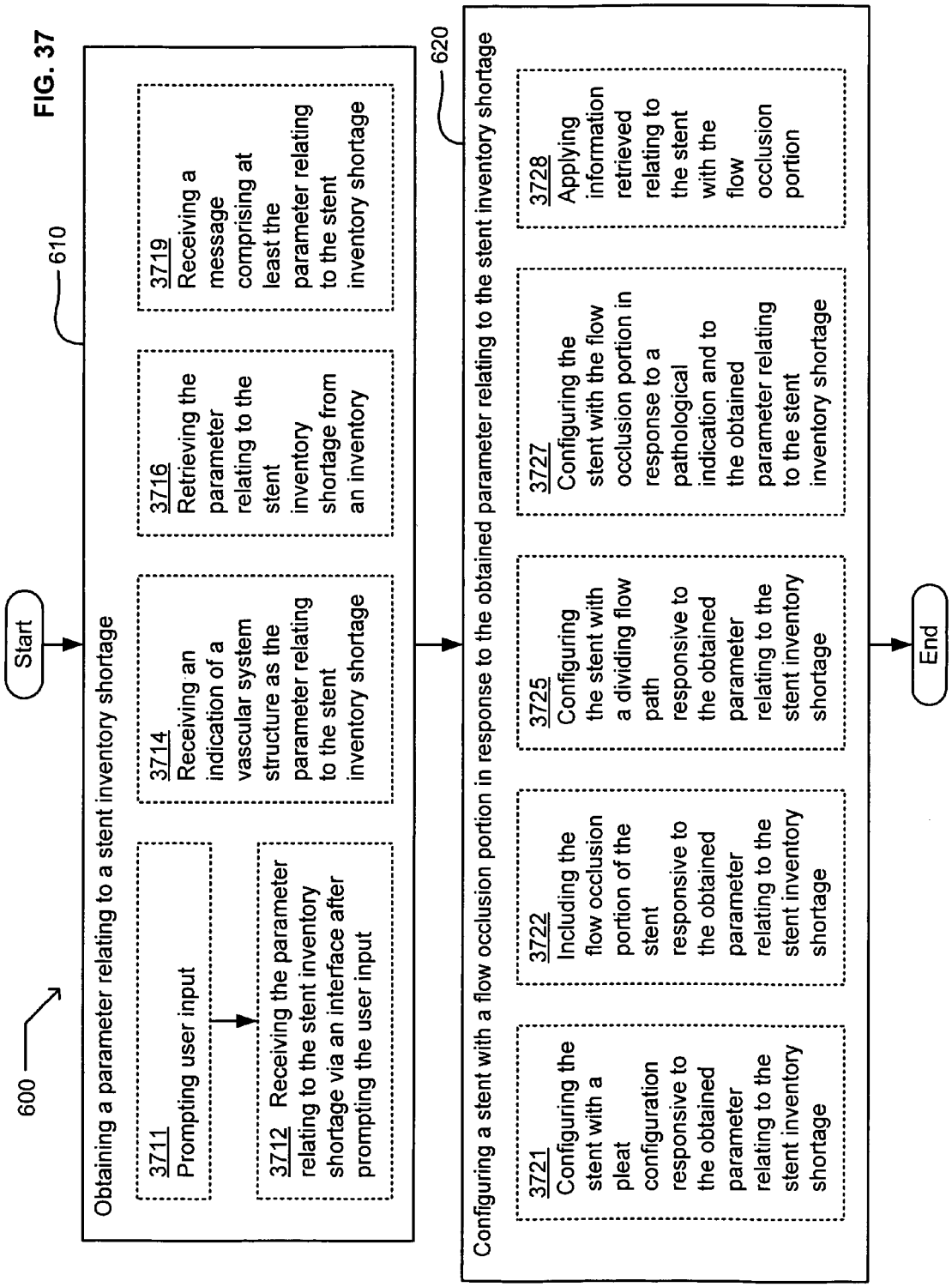

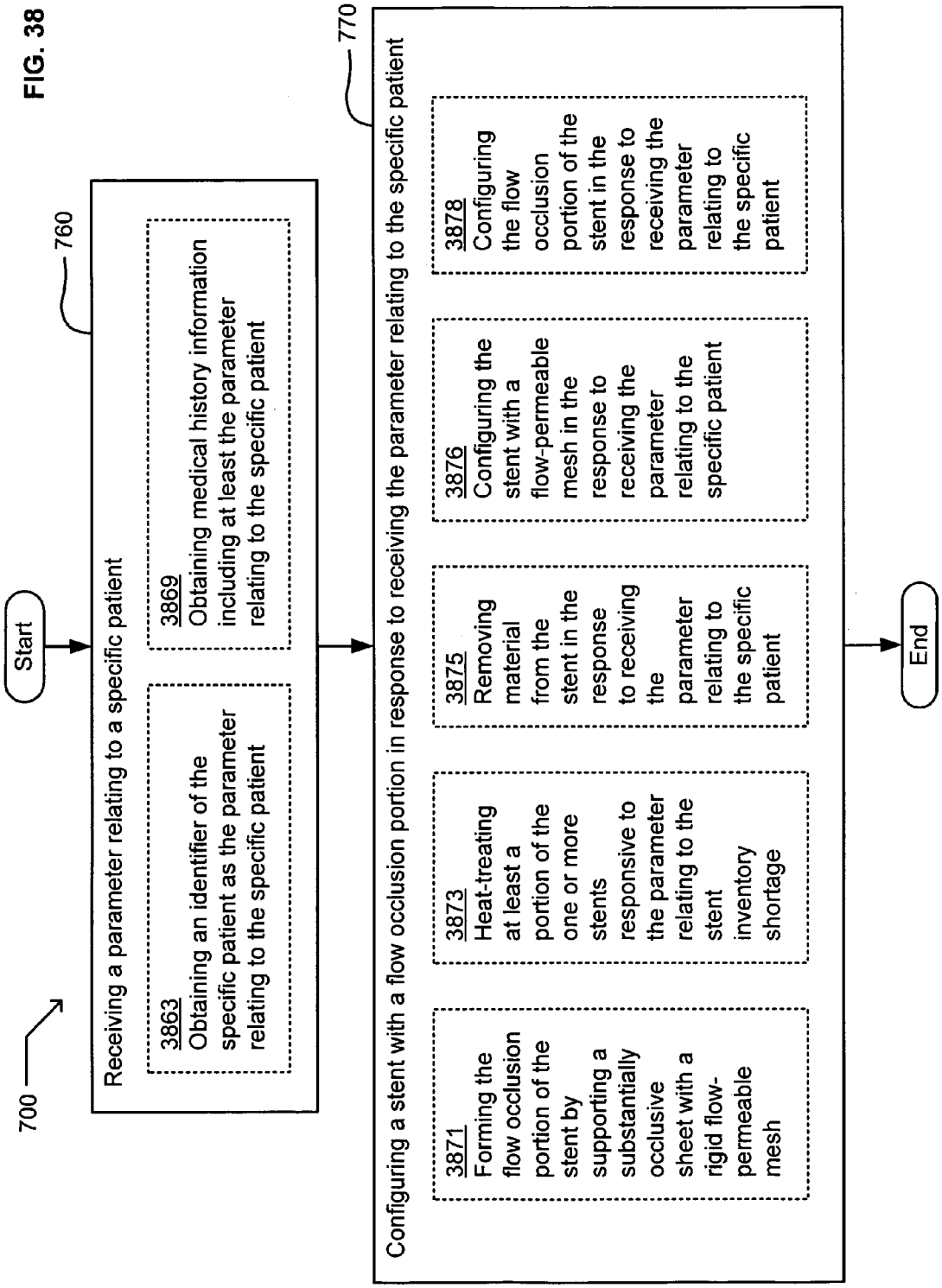

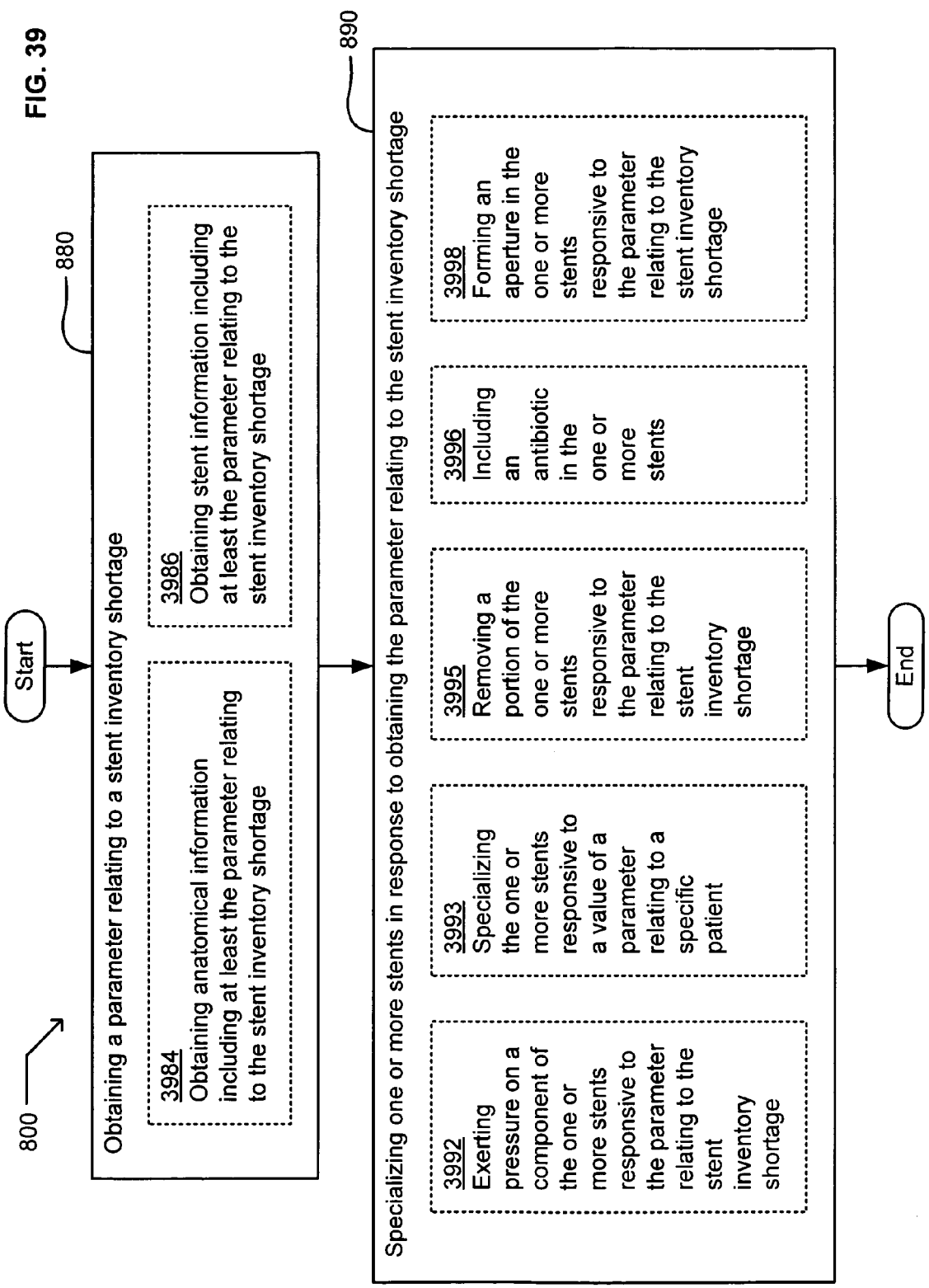

US 8,550,344 B2

SPECIALTY STENTS WITH FLOW CONTROL FEATURES OR THE LIKE

SUMMARY

An embodiment provides a method. In one implementation, the method includes but is not limited to obtaining a parameter relating to a stent inventory shortage and configuring a stent with a flow occlusion portion in response to the obtained parameter relating to the stent inventory shortage. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining a parameter relating to a stent inventory shortage and circuitry for configuring a stent with a flow occlusion portion in response to the obtained parameter relating to the stent inventory shortage. In addition to the foregoing, other system aspects are described in the claims, drawings, and text forming a part of the present disclosure.

An embodiment provides a method. In one implementation, the method includes but is not limited to receiving a parameter relating to a specific patient and configuring a stent with a flow occlusion portion in response to receiving the parameter relating to the specific patient. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for receiving a parameter relating to a specific patient and circuitry for configuring a stent with a flow occlusion portion in response to receiving the parameter relating to the specific patient. In addition to the foregoing, other system aspects are described in the claims, drawings, and text forming a part of the present disclosure.

An embodiment provides a method. In one implementation, the method includes but is not limited to obtaining a parameter relating to a stent inventory shortage and specializing one or more stents in response to obtaining the parameter relating to the stent inventory shortage. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining a parameter relating to a stent inventory shortage and circuitry for specializing one or more stents in response to obtaining the parameter relating to the stent inventory shortage. In addition to the foregoing, other system aspects are described in the claims, drawings, and text forming a part of the present disclosure.

In addition to the foregoing, various other embodiments are set forth and described in the text (e.g., claims and/or detailed description) and/or drawings of the present description.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 4-5 each depict exemplary environments in which one or more technologies may be implemented jonathan

FIG. 17 depicts another stenting site in which one or more technologies may be implemented.

FIGS. 18-19 each depict another view of the stenting site of FIG. 17.

FIG. 34 depicts variants of the flow of FIG. 3.

FIGS. 35-37 depicts variants of the flow of FIG. 6.

FIG. 38 depicts variants of the flow of FIG. 7.

FIG. 39 depicts variants of the flow of FIG. 8.

DETAILED DESCRIPTION

Figure 3:
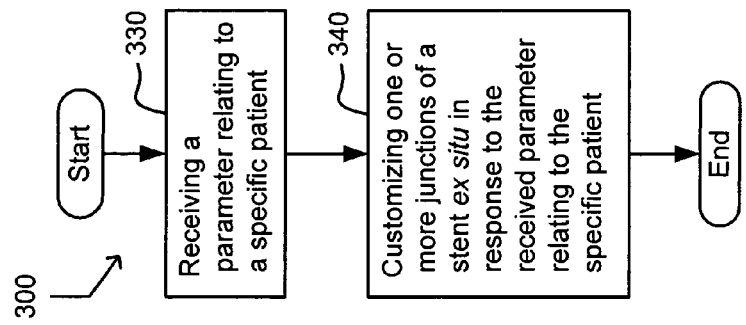
FIG. 3 depicts a high-level logic flow of another operational process.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
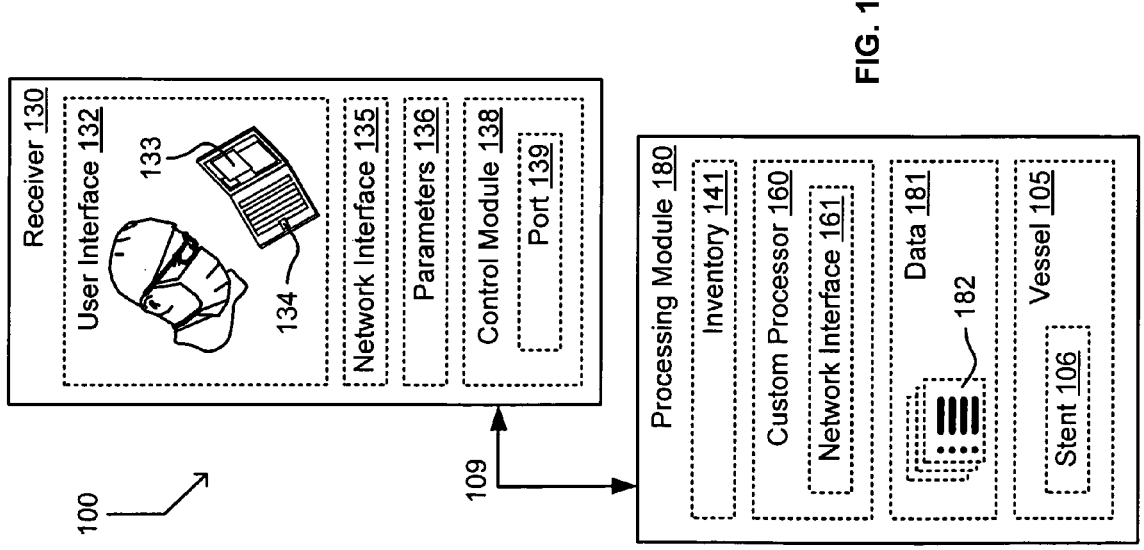
FIG. 1 depicts an exemplary environment in which one or more technologies may be implemented.

Referring now to FIG. 1, there is shown an exemplary environment in which one or more technologies may be implemented. As shown system 100 comprises receiver 130 and processing module 180 operatively coupled by linkage 109. Receiver 130 may include one or more of user interface 132 (e.g. with output device 133 or input device 134), network interface 135 (e.g. in communication with a network, not shown), one or more parameters 136, control module 138 operably configured to control processing module 180 via port 139. Processing module 180 may include one or more of inventory 141, custom processor 160 (optionally with network interface 161), data 181 (optionally including tables 182), and vessel 105 (optionally containing stent 106).

Figure 2:
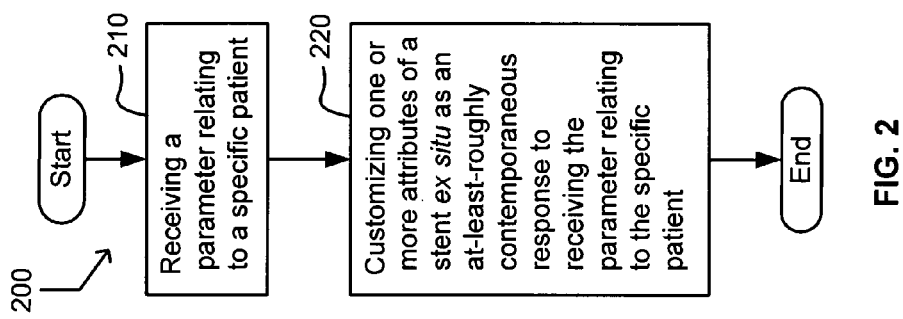
FIG. 2 depicts a high-level logic flow of an operational process.

Referring now to FIG. 2, there is shown a high-level logic flow 200 of an operational process. Operation 210 describes receiving a parameter relating to a specific patient (e.g. receiver 130 receiving one or more of a patient identifier, a patient attribute, a customized stent feature, a handle for obtaining patient information, or the like). In some embodiments, the relation can be revealed or otherwise made accessible by a patient, healthcare provider or other user.

Operation 220 describes customizing one or more attributes of a stent ex situ as an at-least-roughly contemporaneous response to receiving the parameter relating to the specific patient (e.g. processing module 180 making or adapting the stent directly or by proxy within about a month of obtaining the parameter from the specific patient). In some embodiments, a customization or adaptation event can be roughly contemporaneous with receiving a parameter if soon enough so that a substantial physiological change bearing upon the event is unlikely or unexpected. This can encompass as much as a few months or as little as a day in some instances, depending on the patient and the circumstances. Those skilled in the art will recognize, however, that customization or adaptation systems and methods described herein that can take only a few minutes, or sometimes less, which can be especially useful for addressing an arterial perforation or similar emergency as may arise during a surgical procedure.

Referring now to FIG. 3, there is shown a high-level logic flow 300 of another operational process. Operation 330 describes receiving a parameter relating to a specific patient (e.g. receiver 130 receiving one or more of a patient identifier, a patient attribute, a customized stent feature, a handle for obtaining patient information, or the like). In some embodiments, the relation can be revealed or otherwise made accessible by a patient, healthcare provider or other user.

Operation 340 describes customizing one or more junctions of a stent ex situ in response to the received parameter relating to the specific patient (e.g. processing module 180 making or adapting a friction-fit, joint, or adhesion between or along portions of the stent). In some embodiments processing module 180 can be configured to perform one or more operations of other flows taught herein as well, such as those taught in FIGS. 30-39. In some embodiments operation 340 can customize a junction in component form also, such as by ensuring a proper fit between components of a bifurcated stent designed for in situ assembly.

Referring now to FIG. 4, there is shown another exemplary environment in which one or more technologies may be implemented. As shown system 400 includes receiver 430 including one or more of parametric input 410, local interface 432, network interface 435, control module 438, or message parser 450. System 400 optionally couples to one or more implementation system (such as processing module 180 or the system of FIG. 5) via direct linkage 497 or (indirectly) via network linkage 498 and network 496. Parametric input 410 includes one or more of measurement input 411 or model input 412. Model input 412 can include one or more of patient identifier input 413, material identifier input 415, dimensional input 416, image input 418, inventory status input 419, component type input 420, or structure type indicator 421. Component type input 420 can include one or more of stent type input 425, wire type input 426, or sheet type input 427. Structure type indicator 421 can include one or more of vascular type input 422, digestive type input 423, a renal type input (not shown), or some more specific or other categorical information that may assist in effective customization. Local interface 432 can include one or more of output device 433 or input device 434. Control module 438 can optionally include one or more instances of port 439, each of which may control a processing module such as that of FIG. 5, for example, via direct linkage 497 or network linkage 498.

Figure 5:
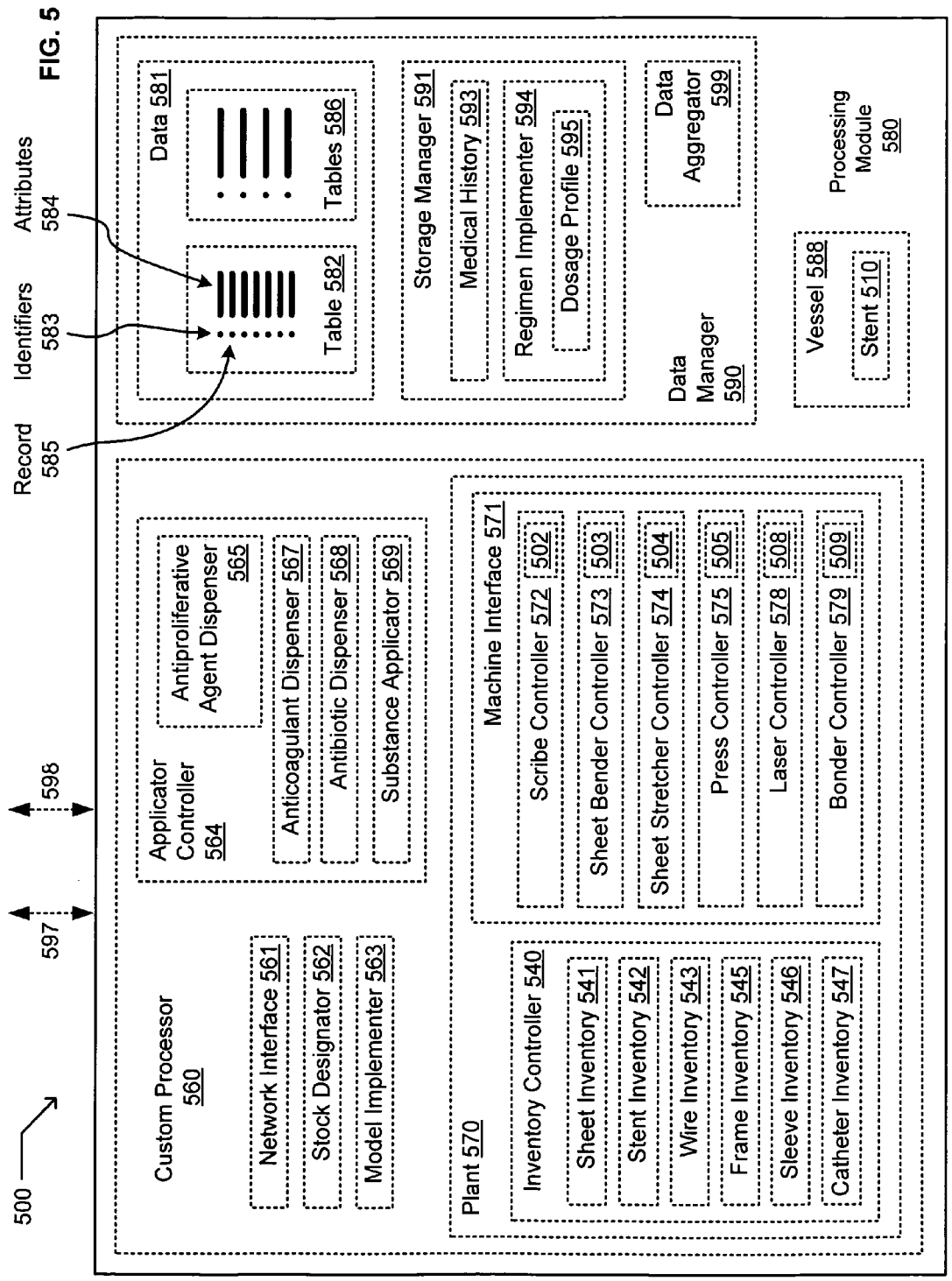

Referring now to FIG. 5, there is shown another exemplary environment in which one or more technologies may be implemented. As shown system 500 includes processing module 580 that can communicate with receiver 430 via direct linkage 597 or network linkage 598. Processing module 580 may contain one or more of custom processor 560, data manager 590, or vessel 588 configured for positioning stent 510 or its components during processing as described herein. In some embodiments, custom processor 560 can include one or more of network interface 561 (operable to interact with linkages 597, 598), stock designator 562, model implementer 563, applicator controller 564, or plant 570. Applicator controller 564 can optionally include or couple with one or more of antiproliferative agent dispenser 565, anticoagulant dispenser 567, antibiotic dispenser 568, substance applicator 569, or the like. Plant 570 can include one or more of inventory controller 540 or machine interface 571. In some embodiments, inventory controller 540 can include or couple with one or more of sheet inventory 541, stent inventory 542, wire inventory 543, frame inventory 545, sleeve inventory 546, or catheter inventory 547. Machine interface 571 can likewise include or couple with one or more of scribe controller 572 operable for controlling scribe 502, sheet bender controller 573 operable for controlling sheet bender 503, sheet stretcher controller 574 operable for controlling sheet stretcher 504, press controller 575 operable for controlling press controller 505, laser controller 578 operable for controlling laser 508, or bonder controller 579 operable for controlling bonder 509. Data manager 590 can include one or more of data 581, storage manager 591, or data aggregator 599. Data 581 can include table 582 containing several instances of record 585 each associating one or more identifiers 583 with one or more attributes 584 as well as other tables 586, as described herein. Storage manager 591 can include one or more of medical history 593 or regimen implementer 594, which can optionally include dosage profile 595.

Those skilled in the art will recognize that connections among instances of components of systems 400, 500 can exist transiently in some embodiments. In one scenario stent 510 can be formed from sheet inventory 541, for example, before being transported to another instance of system 500 at which it is coated by a substance applicator 569 and then compressed into a custom catheter from catheter inventory 547. In this fashion a stent may undergo multiple instances of specialization at various processing sites.

Figure 6:
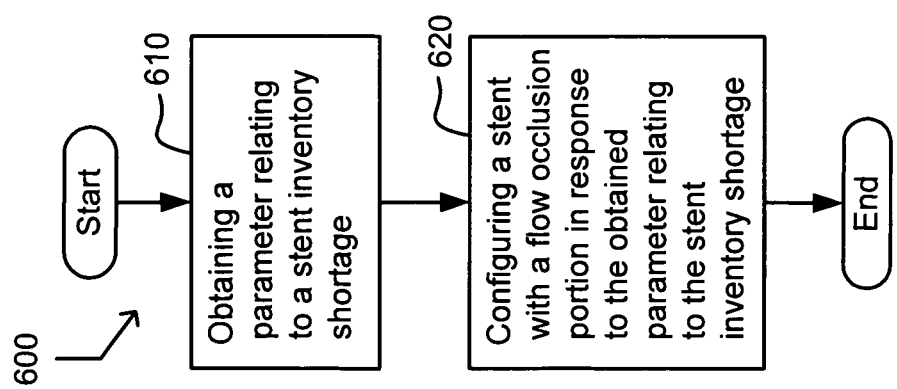
FIG. 6 depicts a high-level logic flow of another operational process.

Referring now to FIG. 6, there is shown a high-level logic flow 600 of another operational process. Operation 610 describes obtaining a parameter relating to a stent inventory shortage (e.g. receiver 130 receiving some quantity, cost, size, composition, configuration, distinguishing identifier or feature, or the like, of a just-designed stent or other stent in short supply). In some embodiments information from several inventories accessible to a requester is used in establishing the stent inventory shortage. Alternatively or additionally, the parameter can be obtained substantially in lieu of other indications of the inventory shortage.

Operation 620 describes configuring a stent with a flow occlusion portion in response to the obtained parameter relating to the stent inventory shortage (e.g. processing module 180 configuring the flow occlusion portion or a frame that supports it responsive to graphical or other positional indications describing a stent in short supply). Alternatively or additionally, the obtained parameter can relate to material compositions, physiological contexts, or other attributes as described herein that may correspond with the material or other shortage. In some embodiments an inventory may include only stent components, for example, that can be combined or otherwise configured in any of a very large array of distinct stent designs. Some such embodiments optionally define no initial inventory of stents with flow occlusion portions, for example, making each stent to order responsive to parameters that distinctly define each flow occlusion portion.

Figure 7:
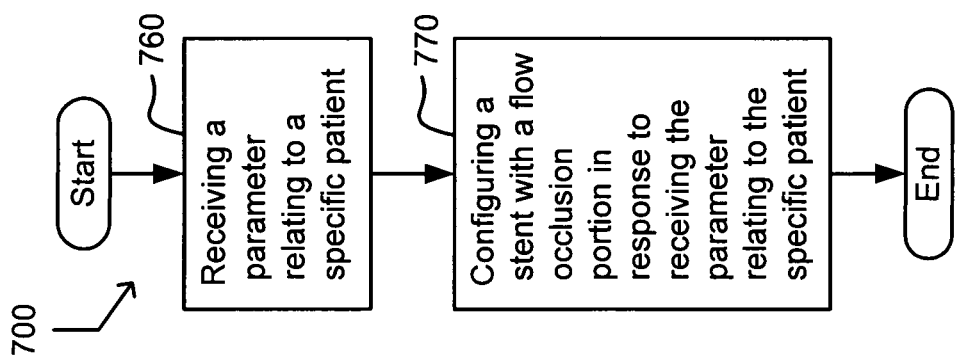
FIG. 7 depicts a high-level logic flow of another operational process.

Referring now to FIG. 7, there is shown a high-level logic flow 700 of another operational process. Operation 760 describes receiving a parameter relating to a specific patient (e.g. receiver 130 receiving one or more of a patient identifier, a patient attribute, a customized stent feature, a handle for obtaining patient information, or the like). In some embodiments, the relation can be revealed or otherwise made accessible by a patient, healthcare provider or other user.

Operation 770 describes configuring a stent with a flow occlusion portion in response to receiving the parameter relating to the specific patient (e.g. processing module 180 forming the flow occlusion portion upon receiving an authorization code from the patient's care facility). In some embodiments, further handshaking occurs in response to receiving the parameter, for example, an outcome of which triggers the stent configuration. Such handshaking can involve, for example, offering a purchaser a choice of catheters in catheter inventory 547.

Figure 8:
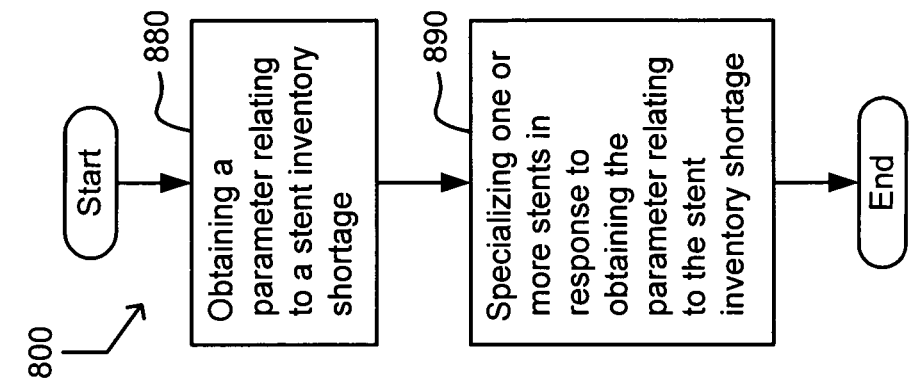
FIG. 8 depicts a high-level logic flow of another operational process.

Referring now to FIG. 8, there is shown a high-level logic flow 800 of another operational process. Operation 880 describes obtaining a parameter relating to a stent inventory shortage (e.g. receiver 130 receiving some quantity, cost, size, composition, configuration, distinguishing identifier or feature, or the like, of a just-designed stent or other stent in short supply). In some embodiments information from several inventories accessible to a requester is used in establishing the stent inventory shortage. Alternatively or additionally, the parameter can be obtained substantially in lieu of other indications of the inventory shortage (e.g. by parameters 156 designating some orders with an "EMERGENCY" status or other parameter indicating an elevated priority.

Operation 890 describes specializing one or more stents in response to obtaining the parameter relating to the stent inventory shortage (e.g. processing module 180 making or adapting several miscellaneous stents to order after receiving the order from a hospital in its vicinity). In some embodiments such stents can each be provided compressed within a respective short catheter from catheter inventory 547. In some embodiments, the short catheters can be customized by components of system 500 in various combinations as taught herein, substantially in the same manner as described with regard to customizing stents.

Figure 9:
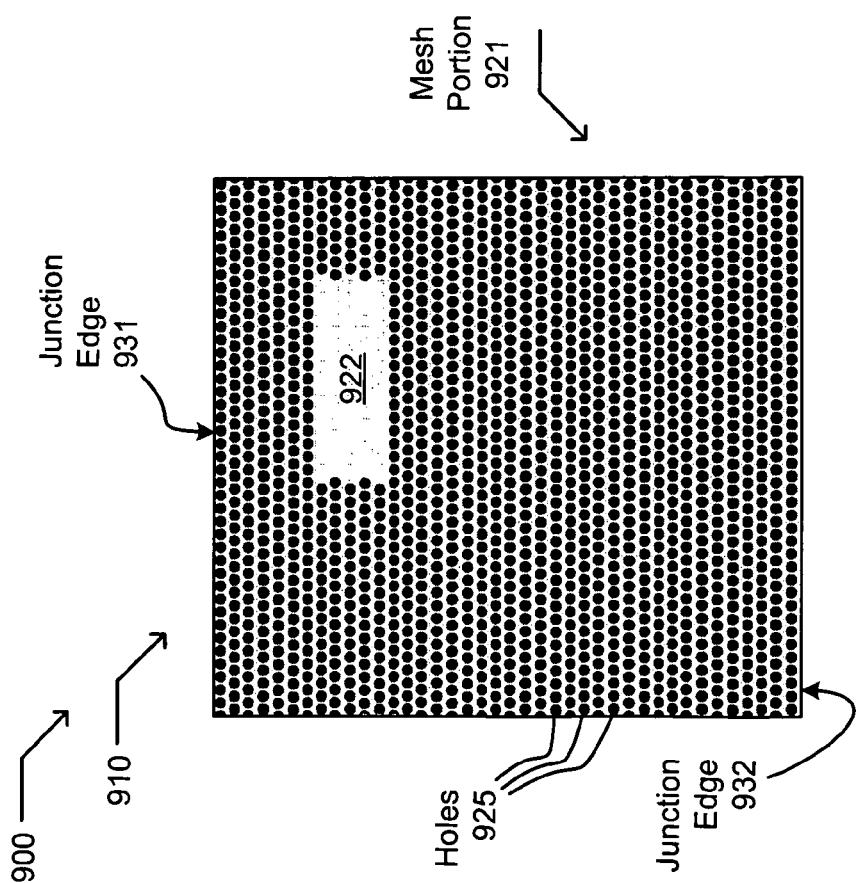
FIG. 9 depicts a stent component in which one or more technologies may be implemented.

Referring now to FIG. 9, there is shown an exemplary environment in which one or more technologies may be implemented. As shown component 900 comprises sheet material 910 in a substantially rectangular form including flexible mesh portion 921 (with numerous holes 925) and flow occlusion portion 922. Sheet material 910 can be formed into a stent by welding, soldering, gluing, or otherwise affixing junction edge 931 substantially along junction edge 932.

Figure 10:
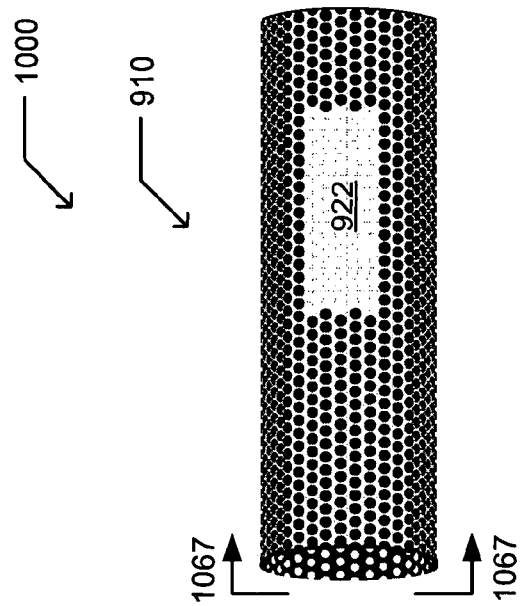
FIG. 10 depicts a stent including the component of FIG. 9.

Referring now to FIG. 10, there is shown another exemplary environment in which one or more technologies may be implemented. As shown stent 1000 comprises sheet material 910 of FIG. 9 rolled into a tube form and bonded as described so that profile 1067 is substantially circular. In some embodiments, a versatile and cost-effective "stent printer" can reside locally within a surgical, veterinary, or other care facility. Inventories of sheet materials and the like can be fed, positioned, or dispensed to form pleats, mesh configurations of a locally controllable density/rigidity, perforations, flow occlusion portions, or the like. Coatings can be formed controllably using toner or inkjet technology, for example, especially for stents with a small number of sheet material components and few junctions like those of FIGS. 9-19.

Figure 11:
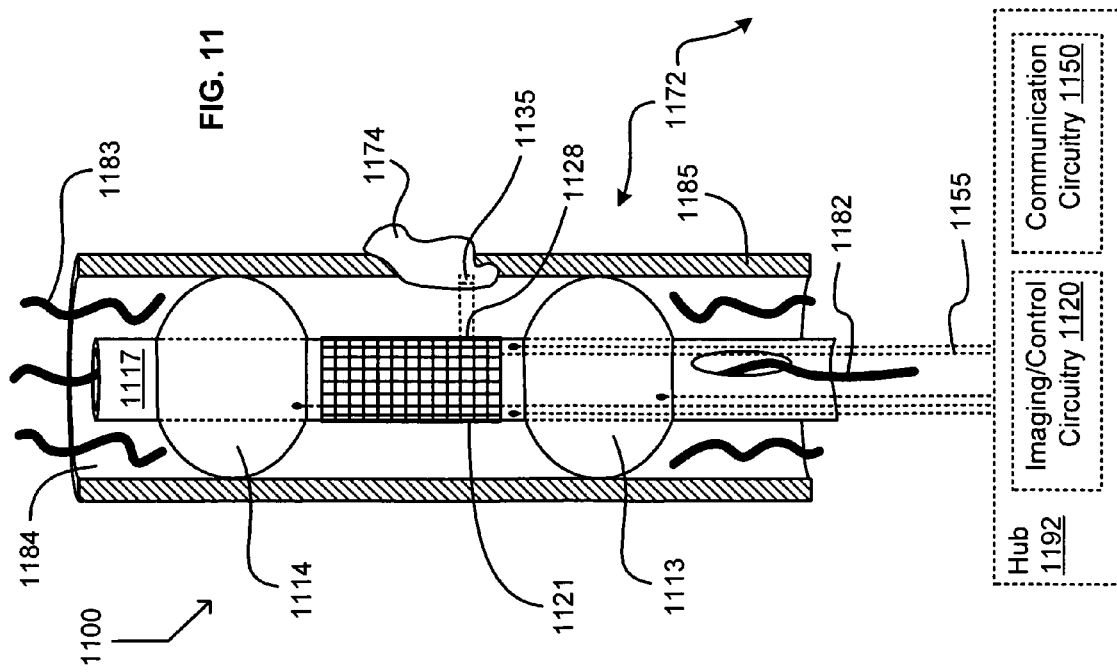
FIG. 11 depicts a stenting site in which one or more technologies may be implemented.

Referring now to FIG. 11, there is shown another exemplary environment in which one or more technologies may be implemented. As shown system 1100 comprises a vascular probe with an intravascular portion 1117 inside blood vessel 1184 of a subject's vascular system. Intravascular portion 1117 can include hub 1192 comprising one or more of imaging/control circuitry 1120 or communication circuitry 1150. In some embodiments, system 1100 includes one or more elements as taught in U.S. patent application Ser. No. 11/414,164 ("Imaging via Blood Vessels"), incorporated by reference to the extent not inconsistent herewith. Blood vessel 1184 is shown in a vicinity of anomaly 1174, with blood 1183 in a flow 1182 through intravascular portion 1117. Anomaly 1174 protrudes somewhat radially from wall 1185 into surrounding tissue 1172. Sensor array 1121 is arranged about the circumference of intravascular portion 1117, including many elements 1128 generally oriented radially. With balloon 1113 and other deflector 1114 deflated, intravascular portion 1117 can easily advance upward using a guidewire until, for example, imaging/control circuitry 1120 can detect anomaly 1174 (via element 1128 and conduit 1155, e.g.). As shown, element 1128 has detected anomaly 1174 within its field of view 1135.

Figure 12:
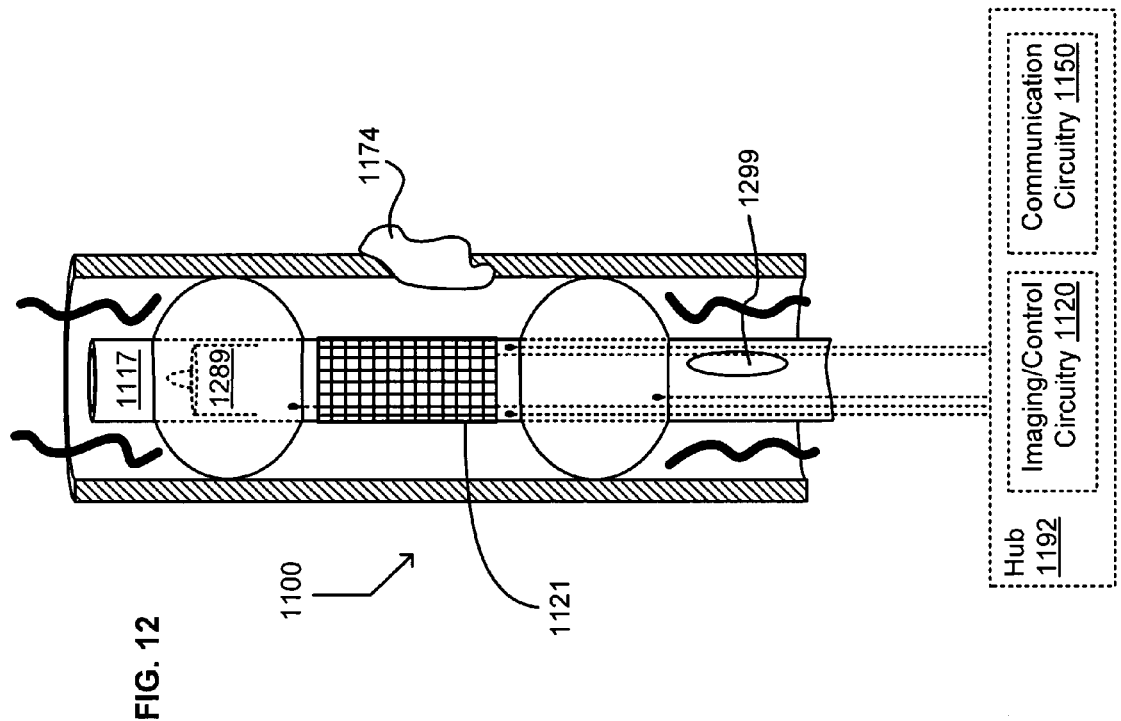
FIGS. 12-14 each depict another view of the stenting site of FIG. 11.

Referring now to FIG. 12, there is shown system 1100 of FIG. 11 in another circumstance. Extension 1289 has entered intravascular portion 1117, substantially closing port 1299 to flow 1182. In some embodiments, hub 1192 can position extension 1289 in a controlled relation to anomaly 1174 by virtue of the imaging from sensor array 1121 and a controlled degree of axial and rotational position of extension 1289.

Figure 13:
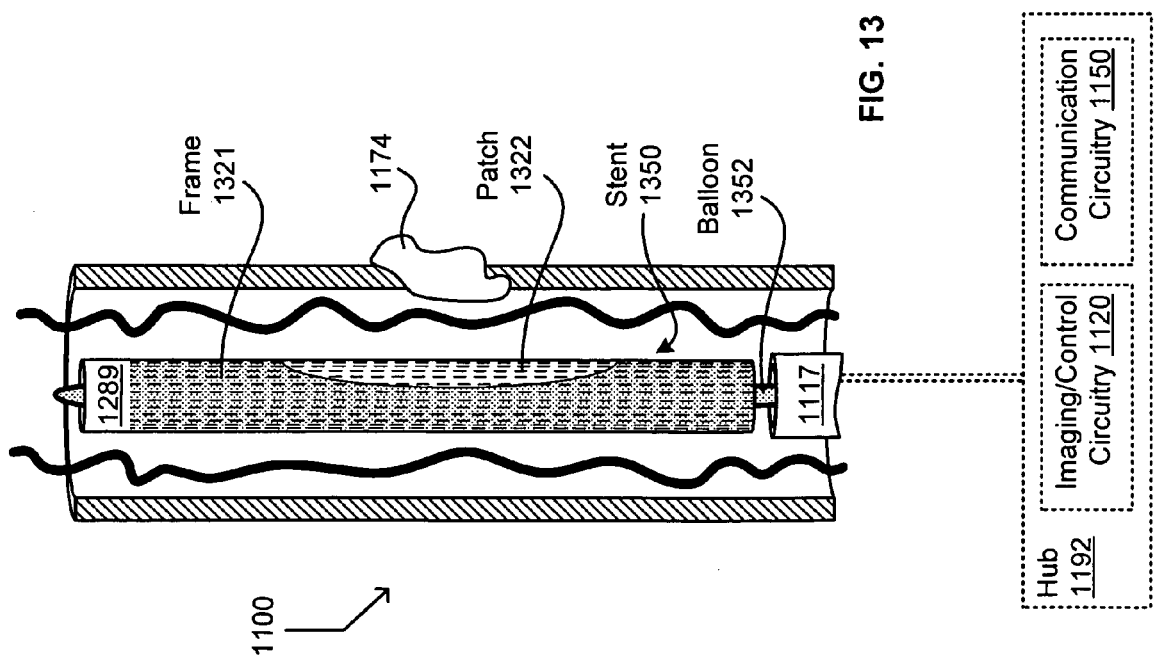

Referring now to FIG. 13, there is shown system 1100 of FIG. 11 in another circumstance. Here, intravascular portion 1117 has been partly withdrawn (downward as shown) to reveal extension 1289 as a collapsed stent 1350 through which balloon 1352 passes. Stent 1350 is positioned distally and rotationally so that patch 1322 substantially aligns with anomaly 1174. A remaining surface (e.g. frame 1321) need not be flow occlusive and can be a sheet material mesh, a wire frame, or the like.

Figure 14:
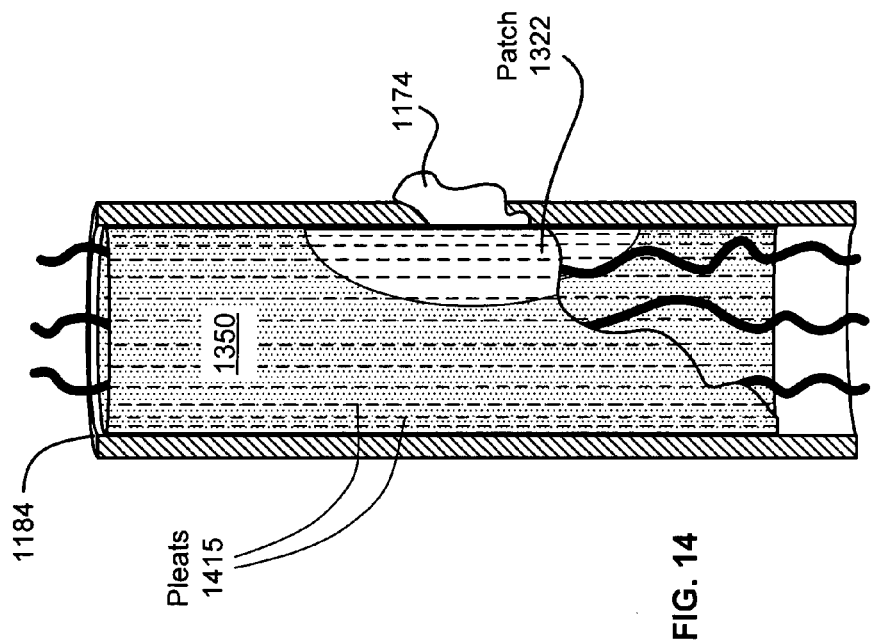

Referring now to FIG. 14, there is shown a partly cut away view of stent 1350 in system 1100 of FIG. 11. As shown, stent 1350 has been expanded by balloon 1352 so that pleats 1415 are each substantially restored to a flat configuration. As shown, patch 1322 aligns over anomaly 1174, substantially reducing flow adjacent anomaly 1174. This general approach can be used to reduce a risk that anomaly 1174 will metastasize, cause a leakage of fluid into or out of vessel 1184, or the like.

Figure 15:
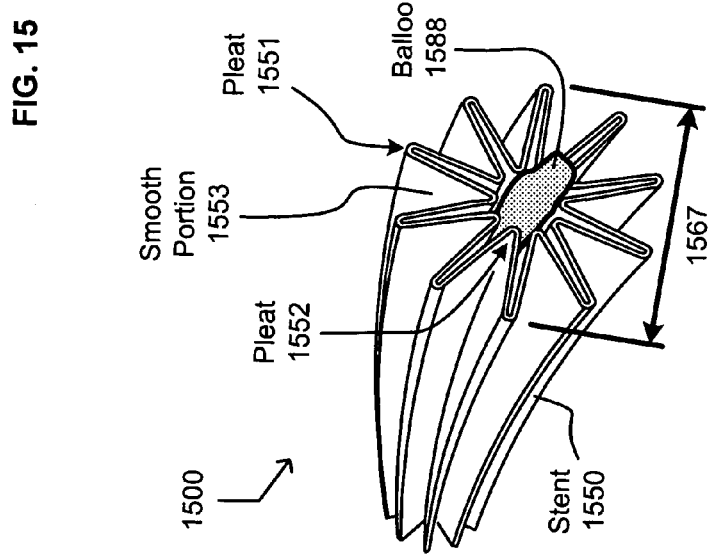
FIG. 15 depicts a system in which one or more technologies may be implemented.

Referring now to FIG. 15, there is shown another exemplary environment in which one or more technologies may be implemented. As shown system 1500 comprises stent 1550 in collapsed form to highlight the use of pleats 1551, 1552 to collapse stent 1550. Each of the pleats is aligned generally axially along stent 1550, joining successive instances of smooth portion 1553 of a sheet material. The effect is so that stent 1550 is collapsed to a diameter 1567 while passing through a catheter and then expanded in situ via balloon 1588 to about twice that diameter.

Figure 16:
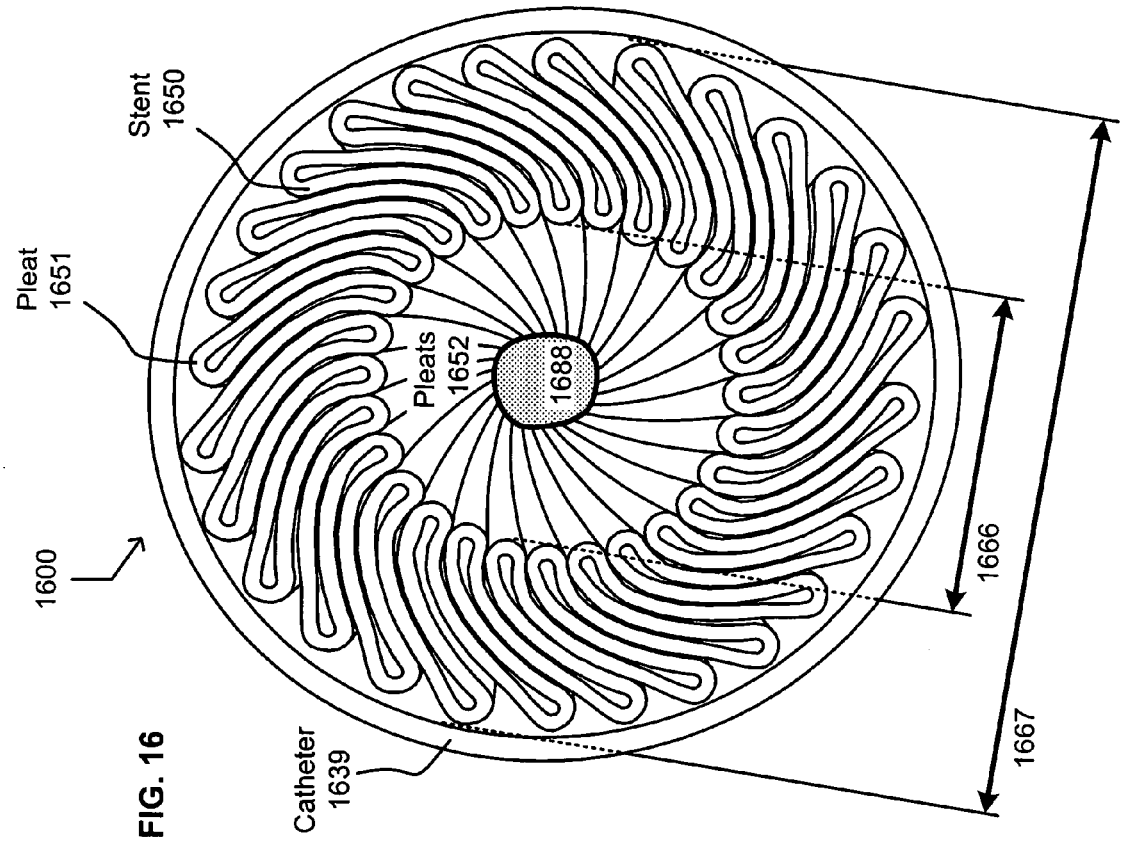
FIG. 16 depicts another system in which one or more technologies may be implemented.

Referring now to FIG. 16, there is shown another exemplary environment in which one or more technologies may be implemented. As shown system 1600 comprises stent 1650 in collapsed form to highlight the use of substantially helical or other curvilinear pleats 1651, 1652 so that stent 1650 can pass through catheter 1639. As shown stent 1650 has been collapsed to a diameter 1667 smaller than one-sixth of its expanded cross-sectional diameter. Even so, an inner diameter 1666 has been maintained at least about 25% as large as diameter 1667 so that balloon 1688 can be urged substantially through stent 1650 before or after collapsing stent 1650.

Referring now to FIG. 17, there is shown a heuristic model 1700 of a forked blood vessel comprising a broad-based aneurysm 1720, an inlet 1701 and two outlets 1702, 1703. As shown, blood flow passes through broad-based aneurysm, creating pressure and a risk of rupture. Moreover the large base makes the aneurysm difficult to treat, for example, by ordinary techniques such as a Guglielmi Detachable Coil (GDC), which can fall out of a broad-based aneurysm and occlude blood vessels. In some embodiments, models such as heuristic model 1700 can be generated (at least initially) by angiography or other imaging technology.

Referring now to FIG. 18, there is shown a model of stent 1800 customized for the forked blood vessel of FIG. 17. Mesh portion 1821 along the top as shown extents from flow inlet 1801 to flow outlet 1802 around (oval-shaped) branch outlet 1803. Flow occlusive portion 1822 similarly extends along the bottom of stent 1800 from flow inlet 1801 to flow outlet 1802. Taper portion 1875 shows a short interval across which diameter of stent 1800 narrows at a perceptible rate (less than 20%, as shown) from a uniform diameter along cylindrical portion 1876. Also a substantial portion of occlusion site 1820 (configured to occlude broad-based aneurysm 1720) has a thrombogenic surface coated or otherwise formed thereon. (In some embodiments, a thrombogenic surface can be one that is more thrombogenic than pure titanium.)

Referring now to FIG. 19, there is depicted a physical environment 1900 in which stent 1800 has been implanted. As shown blood flows from inlet 1901 to outlet 1902 and to outlet 1903, substantially occluded from aneurysm 1920. Also GDC coil 1928 has been implanted into aneurysm 1920, promoting clot formation and minimizing further pressure on the distended tissue of aneurysm 1920.

Figure 20:
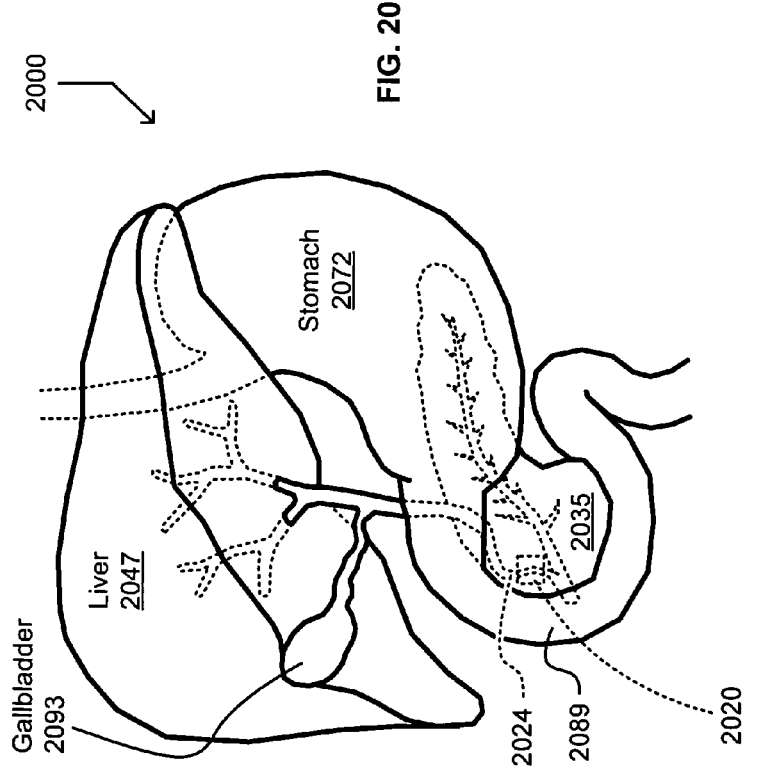
FIG. 20 depicts another stenting site in which one or more technologies may be implemented.

Referring now to FIG. 20, there is shown a heuristic model 2000 of human organs comprising stomach 2072, liver 2047, gallbladder 2093, duodenum 2089, and pancreas 2035. As shown, bile duct 2024 is substantially narrowed in region 2020, creating a risk blockage. Such blockage can interfere with the digestion of fats and can potentially cause jaundice and a variety of other serious problems.

Figure 21:
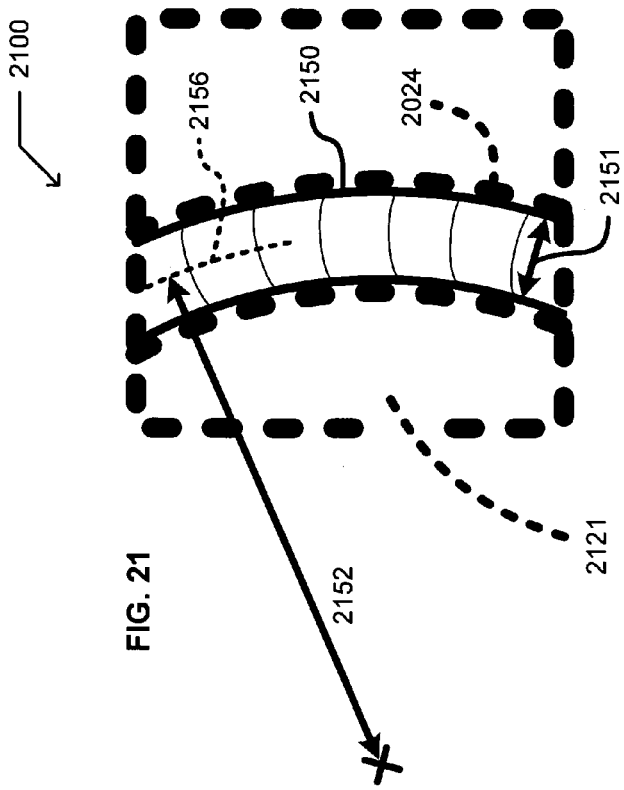
FIG. 21 depicts another view of the stenting site of FIG. 20.

Referring now to FIG. 21, there is shown another exemplary environment in which one or more technologies may be implemented. As shown system 2100 shows a more magnified view 2121 of region 2020 of FIG. 20. Also stent 2150 has been implanted after being customized, for example, with nominal diameter 2151 and radius of curvature 2152 (to a nominal flow path center 2156, e.g.) customized to the specific patient's narrowed portion of bile duct 2024. In some embodiments, an ideal size can be determined by applying a formula to the patient's size, age, gender, symptoms, or the like. An appropriate stent can then be selected for cases in which an off-the-shelf stent provides a satisfactory fit, or customized in other cases.

Figure 22:
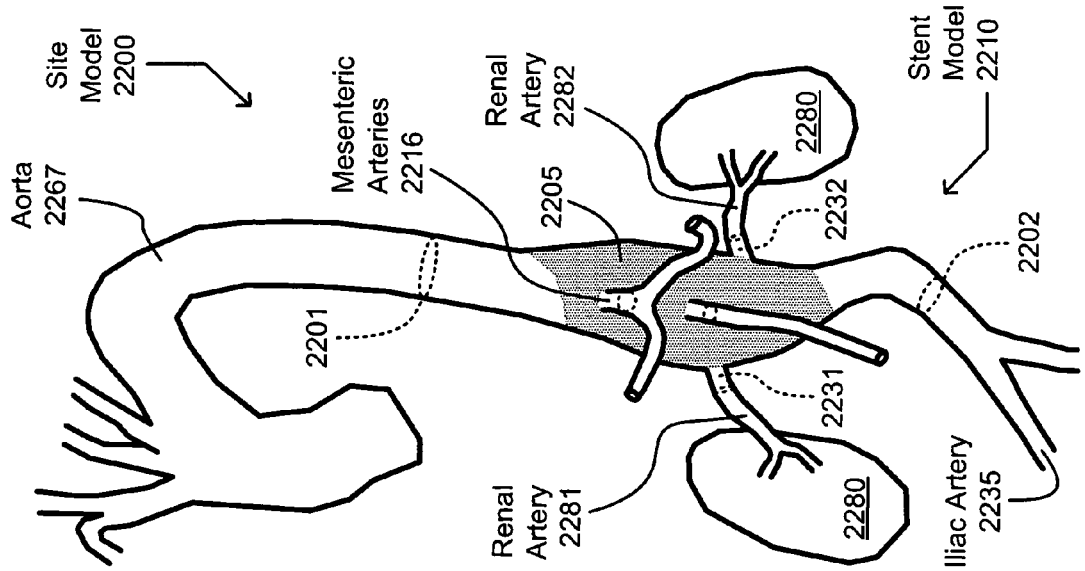
FIG. 22 depicts another stenting site in which one or more technologies may be implemented.

Referring now to FIG. 22, there is shown another exemplary environment in which one or more technologies may be implemented. As shown site model 2200 includes and aorta 2267 with a fusiform abdominal aortic aneurysm 2205, as well as kidneys 2280, and iliac artery 2235 for reference. As shown aorta 2267 presents a very challenging stenting site, in that vital arteries emerge from aneurysm 2205—renal arteries 2281, 2282 and mesenteric arteries 2216—that should not be occluded for very long during implantation. Interruptions in flow to these arteries can damage kidneys 2280, for example. Moreover a rupture of aneurysm 2205 or any flawed stent deployment are serious risks.

In one scenario, site model 2200 is initially received as MRI or similar anatomical data from the specific patient, such as by model implementer 563. Model implementer may likewise recognize aneurysm 2205 and present a default stent model 2210. Alternatively or additionally, a surgeon may provide some stent parameters such as locations of flow port 2201, 2202, such as with a pointing device or by providing a stent model name like "Fusiform Abdominal Aortic M" by which stent model 2210 may be retrieved, adapted, or implemented. In some embodiments, renal arteries 2281, 2282 and mesenteric arteries 2216 are fitted with short sleeves 2231, 2232 as shown, for example, by application of the model or by specification of the surgeon. Alternatively or additionally, local interface 432 may permit a surgeon to signal a succession of the "Fusiform Abdominal Aortic" models graphically, which succession may be accompanied by statistics, supporting literature, components, sources, or the like relating to that model for the surgeon's consideration.

Figure 23:
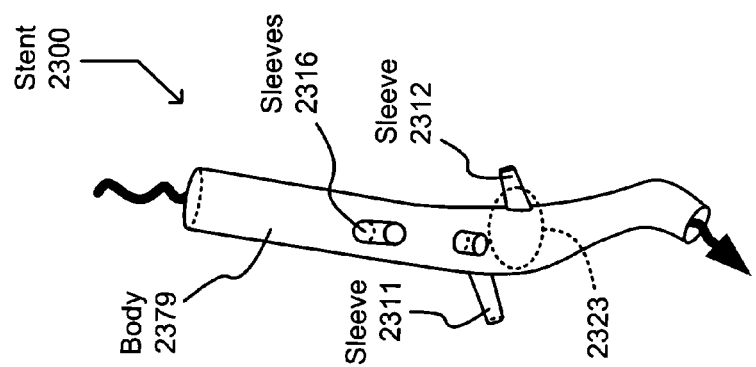

Referring now to FIG. 23, there is shown another exemplary environment in which one or more technologies may be implemented. As shown model stent 2300 comprises body 2379 and sleeves 2311, 2312, 2316 custom suited to site model 2200. For deployment it should be considered how these components can be compresses for passage through, for example, iliac artery 2235 and femoral artery (not shown). Some junctions, such as that shown in region 2323 between sleeve 2312 and body 2379, can be an important design issue for effective deployment.

Figure 24:
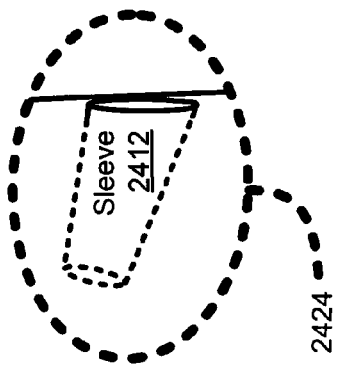
FIGS. 23-25 each depict another view of the stenting site of FIG. 22.

Referring now to FIG. 24, there is shown another exemplary environment in which one or more technologies may be implemented. As shown region 2424 shows a magnified view of region 2323 of FIG. 23. Here, inverted sleeve 2412 illustrates one approach to compressing sleeve 2312 for placement within a catheter (not shown) for a version of stent 2300 that integrates sleeve 2312 and body 2379.

Figure 25:
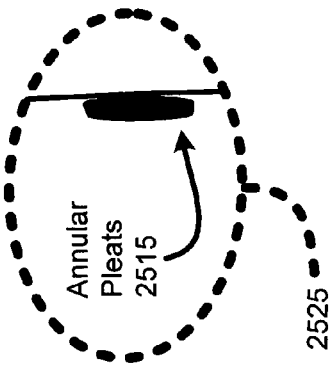

Referring now to FIG. 25, there is shown another exemplary environment in which one or more technologies may be implemented. As shown region 2525 shows another magnified view of region 2323 of FIG. 23. Here, annular pleats 2515 illustrate an alternative approach to compressing sleeve 2312 for placement within a catheter. In some embodiments, annular pleats can be expanded in situ as a bellows. For example, a probe with a guidewire can press through an end of the (initially closed) sleeve 2312 to provide blood flow quickly to kidney 2280 upon deployment. In such a deployment, an imaging system can be used to prevent the guidewire from damaging the aorta 2267 or renal artery 2282.

Figure 26:
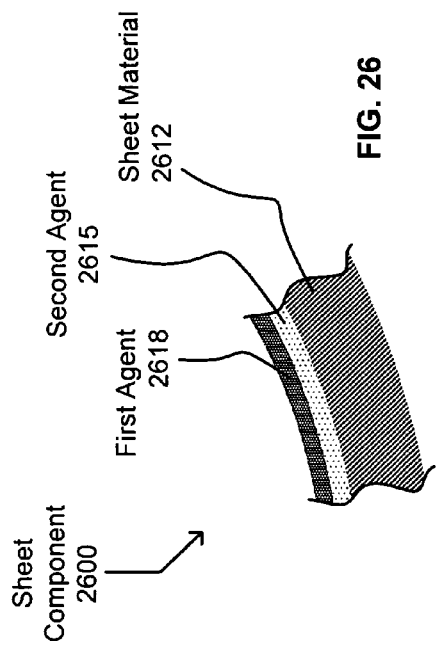
FIG. 26 depicts a stent component in which one or more technologies may be implemented.

Referring now to FIG. 26, there is shown another exemplary environment in which one or more technologies may be implemented. As shown sheet component 2600 includes sheet material 2612 coated with second agent 2615 and first agent 2618 each with a controlled thickness and surface area.

Figure 27:
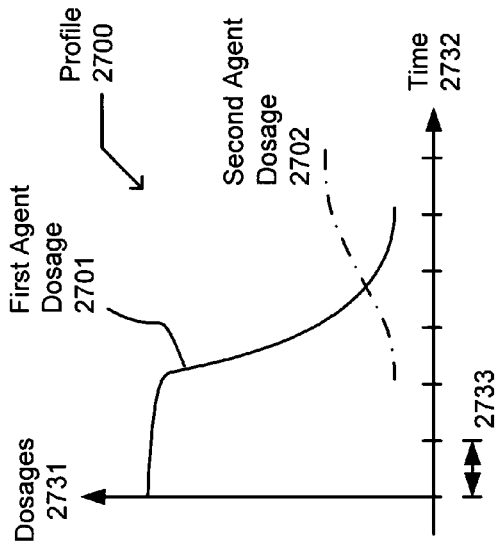
FIG. 27 depicts a profile relating to the stent component of FIG. 26.

Referring now to FIG. 27, there is shown an elution profile 2700 by which (localized) dosages 2731 are schematically plotted against time 2732 in increments 2733 such as days or weeks. As shown, first dosage profile drops off sharply in the third and fourth time increments, during which time second agent dosage 2702 increases steadily. Those skilled in the art will recognize that customizing such drug elution profiles by these teachings can be used as an effective alternative or supplement to systemic regimens that complement the stenting treatment.

Figure 28:
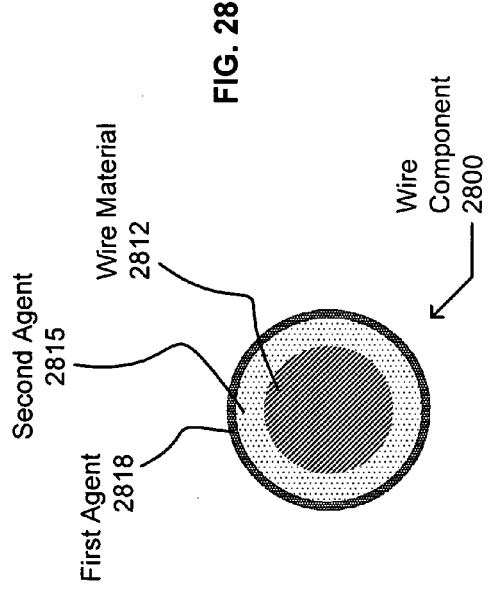
FIG. 28 depicts a stent component in which one or more technologies may be implemented.

Referring now to FIG. 28, there is shown another exemplary environment in which one or more technologies may be implemented. As shown wire component 2800 includes wire material 2812 coated with second agent 2815 and first agent 2818 each with a controlled thickness and surface area.

Figure 29:
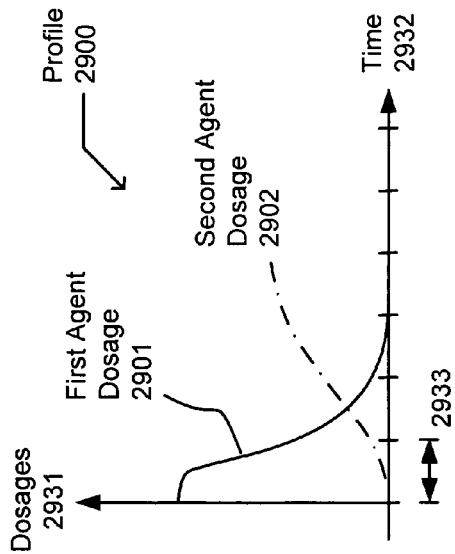
FIG. 29 depicts a profile relating to the stent component of FIG. 28.

Referring now to FIG. 29, there is shown an elution profile 2900 by which (localized) dosages 2931 are schematically plotted against time 2932 in increments 2933 such as days or weeks. As shown, first dosage profile drops off sharply in the first and second time increments, and second agent dosage 2902 increases steadily through the first four increments. Those skilled in the art will recognize that customizing such drug elution profiles by these teachings can be used as an effective alternative or supplement to systemic regimens that complement the stenting treatment.

In some embodiments, first agents 2618, 2818 include one or more of an anticoagulant or antiplatelet and second agents 2615, 2815 include one or more of an antiproliferative. Alternatively or additionally, first agents 2618, 2818 can include an antibiotic. Alternatively or additionally, second agents 2615, 2815 can include a chemotherapy treatment (responsive to an indication of an anomaly that may be cancerous, e.g.). In some embodiments, an elutive customization of one structure is generated in response to an elutive attribute of another structure (e.g. displaying information about an off-the-shelf version of wire component 2800 before receiving a customized regimen for sheet component 2600).

Figure 30:
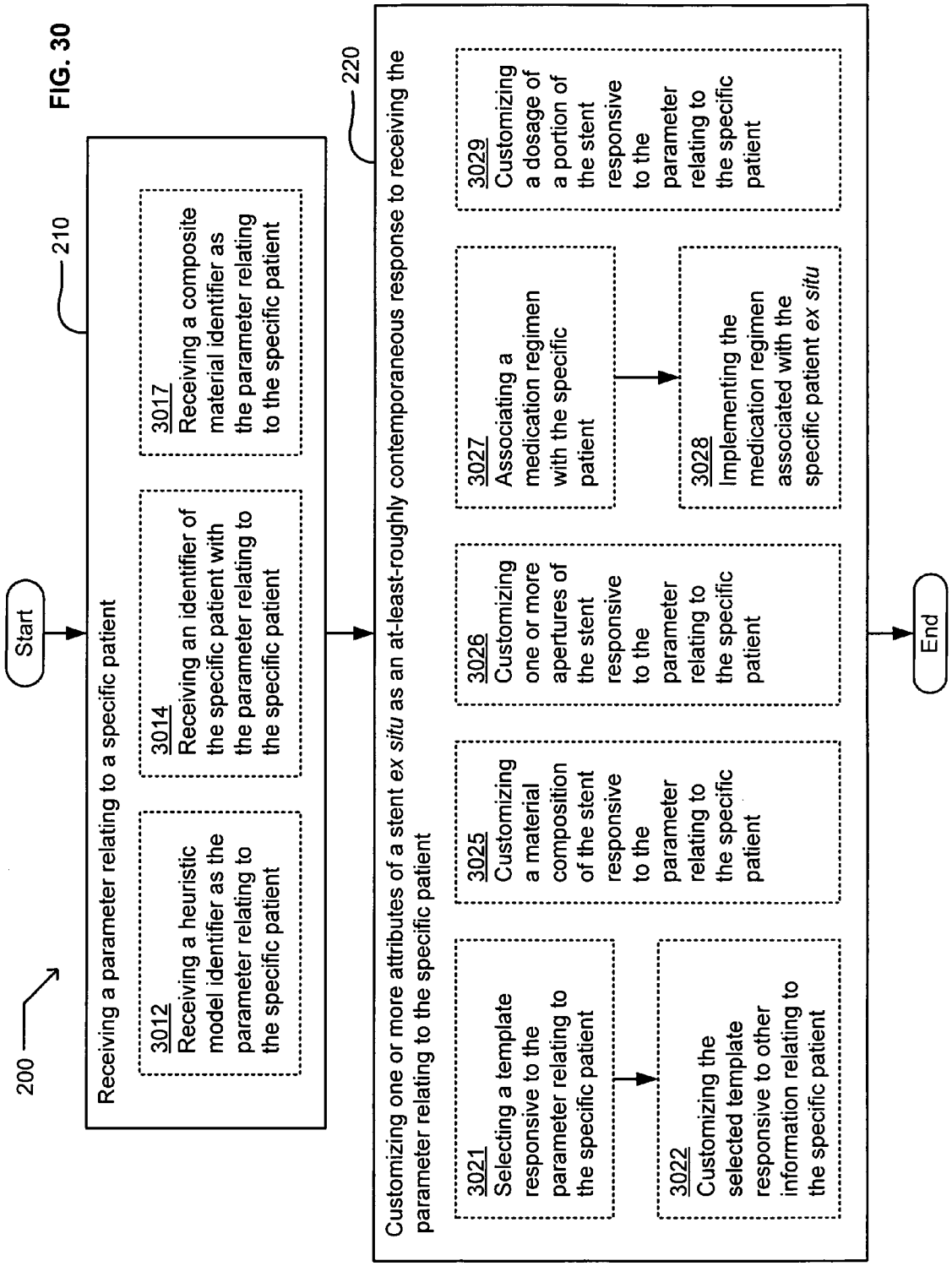
FIGS. 30-33 depict variants of the flow of FIG. 2.

Referring now to FIG. 30, there are shown several variants of the flow 200 of FIG. 2. Operation 210—receiving a parameter relating to a specific patient—may include one or more of the following operations: 3012, 3014, or 3017. Operation 220—customizing one or more attributes of a stent ex situ as an at-least-roughly contemporaneous response to receiving the parameter relating to the specific patient—may include one or more of the following operations: 3021, 3022, 3025, 3026, 3027, 3028, or 3029.

Operation 3012 describes receiving a heuristic model identifier as the parameter relating to the specific patient (e.g. model input 412 receiving a filename or record number of a model of a broad-based aneurysm). The model may call for or utilize parameters such as vessel size, vessel curvature, vessel elasticity, or the like. In some embodiments such parameters can be provided via image input 418 or provided or modified by local interface 432. This can occur, for example, in embodiments in which operation 210 is performed by receiver 430 and in which operation 220 is performed by processing module 580.

Operation 3014 describes receiving an identifier of the specific patient with the parameter relating to the specific patient (e.g. patient identifier input 413 receiving a patient name or number in a common record or message with one or more parameters that may guide stent customization). In some embodiments, the parameter includes a placements site descriptor such as "intracranial," "peripheral vascular," "intraabdominal," "intrathoracic," or the like, or a code corresponding with such a descriptor. Alternatively or additionally the parameter may include or accompany a pathology descriptor such as "AVM" (for an arteriovenous malformation), "fistula," "stenosis," "aneurysm," or the like, for example, for a vascular stent.

Operation 3017 describes receiving a composite material identifier as the parameter relating to the specific patient (e.g. material identifier input 415 identifying nitinol or other titanium-containing alloy relating to a stent component). Alternatively or additionally, material identifier input 415 can identify a second layer such as a silver-containing plating on a sheet material or wire material as the stent component.

Operation 3021 describes selecting a template responsive to the parameter relating to the specific patient (e.g. stock designator 562 selecting a sheet material as a thinnest template that is thick enough or a thickest template that is thin enough). In some instances, a plating, texturing, or other template surface property can affect template selection as well.

Operation 3022 describes customizing the selected template responsive to other information relating to the specific patient (e.g. sheet stretcher controller 574 stretching at least a portion of the designated stock to obtain a desired thinness with sheet stretcher 504). In some instances, mechanical manipulations of operation 3022 are delayed until a specific instruction or other confirmatory action from a buyer or user is detected. Alternatively or additionally, press controller 575 or other portions of machine interface 571 can perform operation 3022.

Operation 3025 describes customizing a material composition of the stent responsive to the parameter relating to the specific patient (e.g. applicator controller 564 applying one or more coatings of a heparinoid via anticoagulant dispenser 567, responsive to a bleeding risk such as a brain tumor or history of gastrointestinal bleeding). In some instances, a user may signal an anticoagulant application in lieu of explicitly entering such a diagnosis. Alternatively or additionally, a less-specific pathology such as "cannot safely receive systemic anticoagulation" can be interpreted in a like fashion.

Operation 3026 describes customizing one or more apertures of the stent responsive to the parameter relating to the specific patient (e.g. laser controller 578 implementing a stent in a convergent flow path, such as in a vein). Alternatively or additionally, one or more divergent flow paths can be facilitated such as by branch outlet 1803 of stent 1800 of FIG. 18.

Operation 3027 describes associating a medication regimen with the specific patient (e.g. regimen implementer 594 signaling a structure with a long-lasting antiproliferative agent responsive to a medical history 593 indicating the patient's risk of vascular stenosis from stenting). In some embodiments the antiproliferative agent can be covered at first with an antiplatelet agent or an antibiotic.

Operation 3028 describes implementing the medication regimen associated with the specific patient ex situ (e.g. regimen implementer 594 generating a recipe for a succession of medication-containing coatings responsive to user-input dosage profiles like those of FIGS. 27 & 29. In some embodiments a user selects from a variety of defined dosage profiles of therapeutic agents such as angiogenic agents, anti-inflammatories, anti-leukocytes, antilymphocytes, antimitotics, antioxidants, antiproliferatives, anti-restenotics, beta blockers, cardio protectants, hormones, hypertension drugs, immunosuppressants, retinoids, statins, thrombolytics, vasoactive agents, or the like.

Operation 3029 describes customizing a dosage of a portion of the stent responsive to the parameter relating to the specific patient (e.g. dosage profile 595 indicating a specific coating pattern that is thicker and more strongly bonded in a case for which a patient needs a therapeutic agent that can last for several months or more). In some instances, dosage profile 595 can supplement the stent's therapeutic agent with a systemic application of the agent. In other instances, a systemic application of the therapeutic agent can be reduced or omitted so long as a stent will continue to administer the therapeutic agent.

Figure 31:
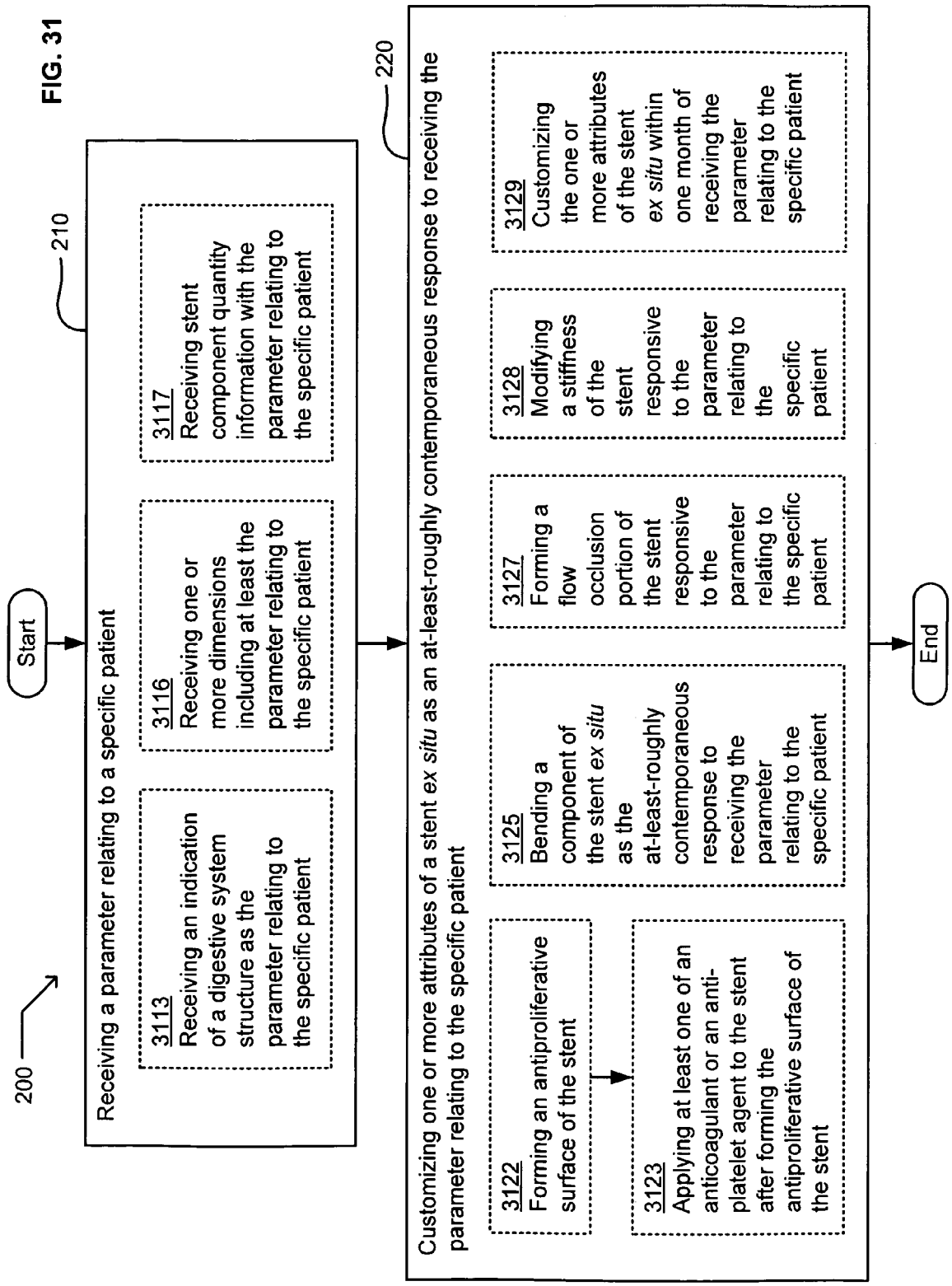

Referring now to FIG. 31, there are shown several variants of the flow 200 of FIG. 2 or 30. Operation 210—receiving a parameter relating to a specific patient—may include one or more of the following operations: 3113, 3116, or 3117. Operation 220—customizing one or more attributes of a stent ex situ as an at-least-roughly contemporaneous response to receiving the parameter relating to the specific patient—may include one or more of the following operations: 3122, 3123, 3125, 3127, 3128, or 3129.

Operation 3113 describes receiving an indication of a digestive system structure as the parameter relating to the specific patient (e.g. digestive type input 423 indicating "yes" responsive to a stenting site in the digestive system as shown in FIG. 20). In some embodiments such a type may cause a stent to be customized with one or more of an antibiotic, a larger flexibility, or a chemically inert surface, for example. In some instances the digestive type input can likewise be recorded in the specific patient's medical history to indicate what kind of stent was used or what caused that kind of stent to be used, for example to track a stent failure rate by context.

Operation 3116 describes receiving one or more dimensions including at least the parameter relating to the specific patient (e.g. dimensional input 416 receiving a diameter of anomaly 1174 as seen by sensor array 1121). In some embodiments, a heuristic model of a round anomaly with a defined center and diameter sufficiently characterizes an occlusion target so that further shape information need not be obtained.

Operation 3117 describes receiving stent component quantity information with the parameter relating to the specific patient (e.g. inventory status information 419 indicating that the stent includes patch 1322 as a component). This can facilitate costing, insurance coverage, inventory adjustment, or the like when and if stent 1350 is constructed physically.

Operation 3122 describes forming an antiproliferative surface of the stent (e.g. applicator controller 564 applying a compound containing the antiproliferative(s) onto the stent via antiproliferative agent dispenser 565). In some embodiments, the antiproliferative surface of a stent body is covered by one or more additional layers such as those of FIGS. 26 & 28.

Operation 3123 describes applying at least one of an anticoagulant or an anti-platelet agent to the stent after forming the antiproliferative surface of the stent (e.g. applicator controller 564 applying an anticoagulant-containing mixture onto a coated stent via anticoagulant dispenser 567). In the embodiment of FIG. 26, for example, a relatively thin layer of antiproliferative is applied to sheet material 2612 (by dipping or spraying, e.g.) as second agent 2615. The first agent 2618 can optionally be applied afterward to at least a portion of second agent 2615.

Operation 3125 describes bending a component of the stent ex situ as the at-least-roughly contemporaneous response to receiving the parameter relating to the specific patient (e.g. sheet bender controller 573 implementing a pleating pattern like that of FIG. 15 with sheet bender 503 to fit stent 1550 into a catheter larger than diameter 1567, responsive to an indication that such a catheter is or will be used for the specific patient). Alternatively or additionally, operation 3125 can be performed upon a heuristic model, such as by model implementer 563. In some embodiments, more than ten pairs of pleats are used to fit a large stent through a selected catheter.

Operation 3127 describes forming a flow occlusion portion of the stent responsive to the parameter relating to the specific patient (e.g. press controller 575 forming few or no openings in flow occlusion portion 1821 while making stent 1800). In some embodiments, stamp controller 575 simultaneously forms other structural features of stent 1800 such as pleats, flow holes, pliability holes (e.g. holes 925 of FIG. 9).

Operation 3128 describes modifying a stiffness of the stent responsive to the parameter relating to the specific patient (e.g. sheet stretcher controller 574 can reduce a stiffness of a sheet material 910 or sheet material 2612 with sheet stretcher 504, responsive to an indication that the unstretched stock is too stiff). Alternatively or additionally, pliability-enhancing holes (such as those of FIG. 9) or etching or machining or the like can be used for a similar reduction of stiffness.

Operation 3129 describes customizing the one or more attributes of the stent ex situ within one month of receiving the parameter relating to the specific patient (e.g. model implementer 563 adapting a defined stent responsive to one or more of patient identifier input 413, material identifier input 415, image input 418, validations, or the like responsive to expert guidance from various specialists who provide the input data at various times). In various embodiments, an least an initial customization can be performed within a narrower interval—e.g. within one week, within one day, within one hour, or within about ten minutes of measuring or otherwise receiving the parameter. After the initial customization, of course, a virtual or physical stent may be completed, retrofitted, updated, further customized, or the like, within the scope of these teachings.

Operation 3211 describes retrieving a record including at least the parameter relating to the specific patient (e.g. network interface 435 requesting a medical history or other record transfer from a remote data source, not shown). Alternatively or additionally, the retrieval can include a roughly contemporaneous completion deadline, a diagnosis, an angiographic reconstruction, or the like.

Figure 32:
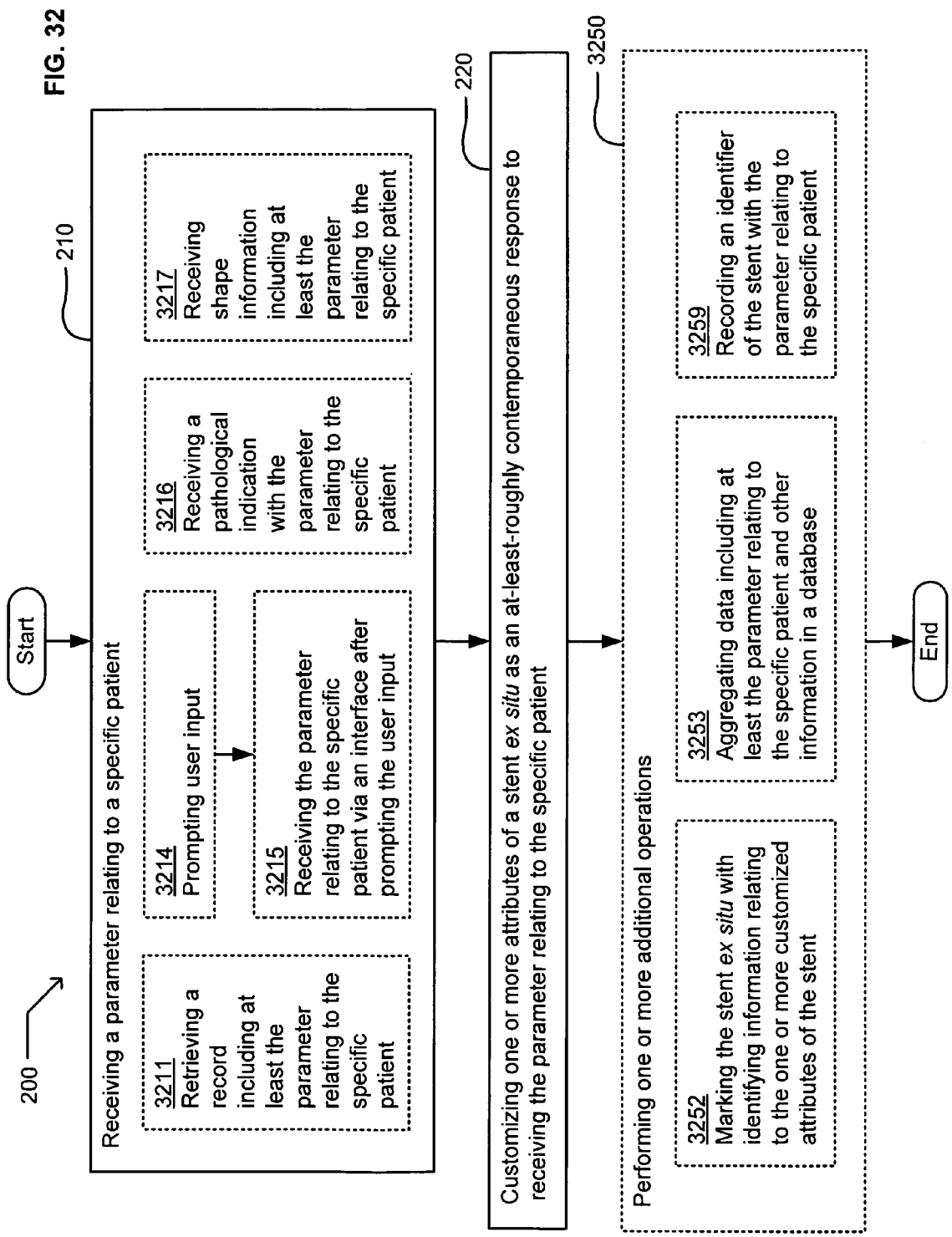

Referring now to FIG. 32, there are shown several variants of the flow 200 of FIG. 2, 30, or 31. Operation 210—receiving a parameter relating to a specific patient—may include one or more of the following operations: 3211, 3214, 3215, 3216, or 3217. Operation 3250 describes performing one or more additional operations (e.g. machine interface 571 compressing the customized stent into an off-the-shelf catheter segment). In some embodiments, operation 3250 can include further aspects of customization, billing, shipping, quality control, material inventory control, component testing, market trends, field performance tracking, regulatory compliance, or the like, for example. In some embodiments, operation 3250 may include one or more of the following operations: 3252, 3253, or 3259.

Operation 3214 describes prompting user input (e.g. output device 133 or the like prompting an input from a surgeon or other information provider). In some instances, output device can comprise a display screen or audio interface in a user environment, for example.

Operation 3215 describes receiving the parameter relating to the specific patient via an interface after prompting the user input (e.g. input device 134 or the like receiving a patient name or status as the parameter relating to the specific patient). In some instances, the parameter can take a default value directly from an MRI or similar data gathering device, responsive to a lack of response from an emergency room doctor. A stent customization can thus occur, in some embodiments, as a direct response to a patient need and without any contemporaneous participation by a care provider.

Operation 3216 describes receiving a pathological indication with the parameter relating to the specific patient (e.g. message parser 450 receiving a medical history or the like indicating that the specific patient has been diagnosed with cholangiocarcinoma). In some embodiments, such an indication can bear toward a stent with a local chemotherapy regimen, for example.

Operation 3217 describes receiving shape information including at least the parameter relating to the specific patient (e.g. dimensional input 416 receiving several three dimensional models from MRI readings, showing how a shape of a segment of specific patient's basilar artery changes during a heartbeat). In some embodiments dimensional input 416 is received as an automatically generated default stent design enabling a surgeon to review and alter the design before providing an authorization to build the actual stent.

Operation 3252 describes marking the stent ex situ with identifying information relating to the one or more customized attributes of the stent (e.g. scribe controller 572 identifying a model or serial number of "XLT259" in an X-ray readable form with scribe 502). In some embodiments a portion of this number signify a material, structure, or subcomponent manufacturer explicitly (such as the "T" signifying titanium in this example). In some embodiments the number can be related to a customized component, for example, by including record 585 linking that identifier with one or more attributes (such as a sheet thickness) in table 582.

Operation 3253 describes aggregating data including at least the parameter relating to the specific patient and other information in a database (e.g. data aggregator 599 archiving stent manufacturing records with a patient or stent identifier). In some embodiments the records can include drug or material sources, exact dimensions, date and place of manufacture, stent designer, patient, intended site, caregiver, or the like. Alternatively or additionally, some of this information may be written explicitly on the stent. Such information can later be correlated with stent failures, for example.

Operation 3259 describes recording an identifier of the stent with the parameter relating to the specific patient (e.g. storage manager 591 recording a custom stent serial number or specification in medical history 593). In some embodiments the medical history 593 can further indicate a custom stent order date, a stent shipment date, or other contemporaneous patient information including the parameter(s) affecting customization.

Figure 33:
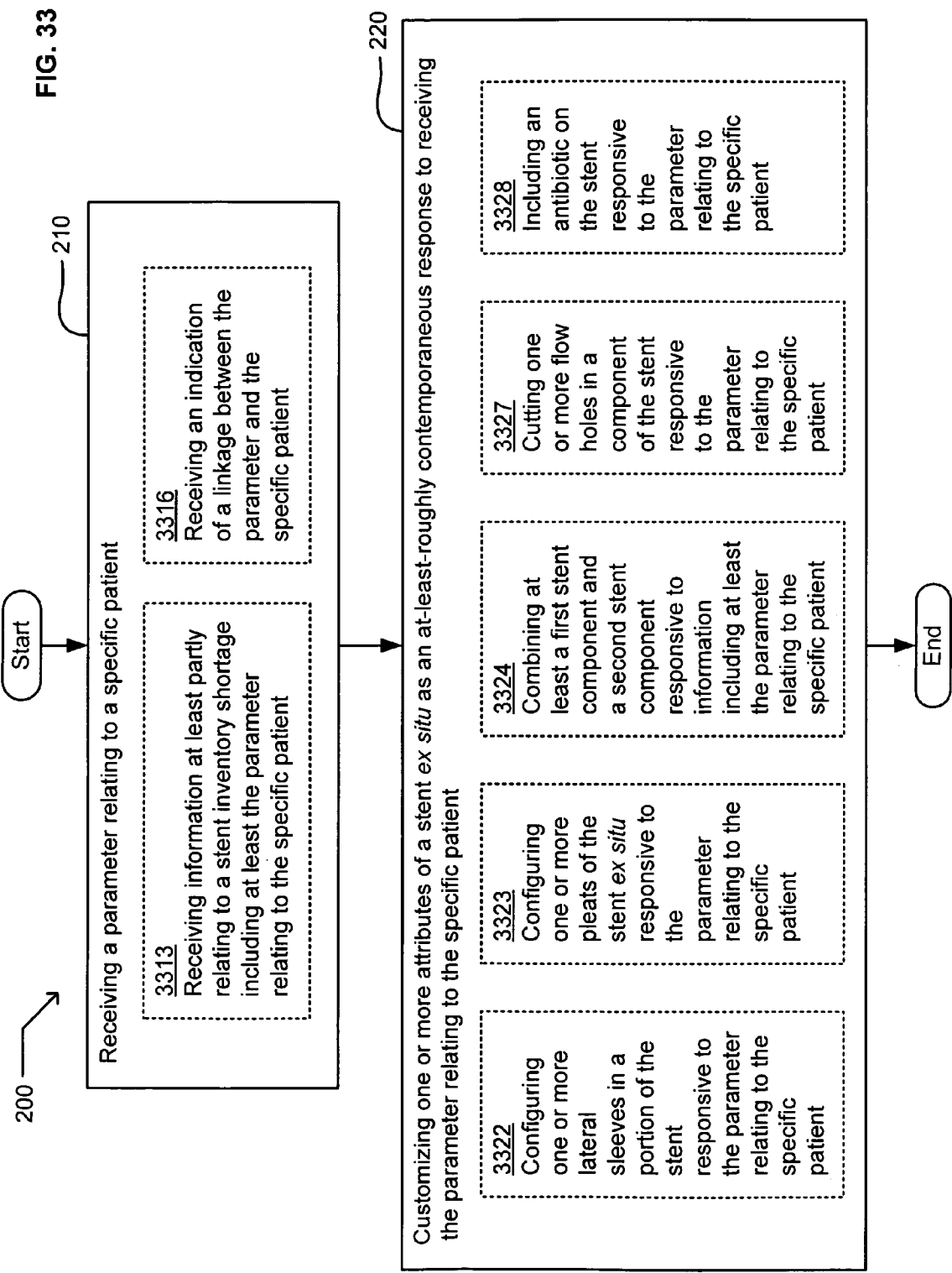

Referring now to FIG. 33, there are shown several variants of the flow 200 of FIG. 2, 30, 31, or 32. Operation 210—receiving a parameter relating to a specific patient—may include one or more of the following operations: 3313 or 3316. Operation 220—customizing one or more attributes of a stent ex situ as an at-least-roughly contemporaneous response to receiving the parameter relating to the specific patient—may include one or more of the following operations: 3322, 3323, 3324, 3327, or 3328.

Operation 3313 describes receiving information at least partly relating to a stent inventory shortage including at least the parameter relating to the specific patient (e.g. inventory status input 419 and stent type input 425 jointly receiving indications that a surgeon wants stent models A, B, and C for a specific patient, and that stent model B is not in stock). In some embodiments the arrival of the stent type input 425 via message parser 450 triggers an automatic inquiry for inventory status input 419, for example.

Operation 3316 describes receiving an indication of a linkage between the parameter and the specific patient (e.g. message parser 450 receiving a record indicating that patient Greg Johnson had an abnormally high blood pressure reading on April 17). In this instance, patient identifier input 413 can identify Greg Johnson, for example with a patient number or the like. The parameter can be "HBP" or a numeric measurement of blood pressure as measurement input 411 or the like.

Operation 3322 describes configuring one or more lateral sleeves in a portion of the stent responsive to the parameter relating to the specific patient (e.g. model implementer 563 generating stent model 2210 including sleeve 2231 and sleeve 2232 responsive to an angiographic reconstruction including site model 2200). In some embodiments bonder controller 579 performs operation 3322 by applying a portion of stent model 2210 to sleeve inventory 546 to affix sleeve 2311 and sleeve 2312 physically to stent body 2379.

Operation 3323 describes configuring one or more pleats of the stent ex situ responsive to the parameter relating to the specific patient (e.g. sheet bender controller 573 applying stent model 2210 to form annular pleats 2515 with sheet bender 503). In other embodiments, sheet bender controller 573 can configure pleat 1651 and pleat 1652 in the configuration of FIG. 16 responsive at least to outer diameter 1667.

Operation 3324 describes combining at least a first stent component and a second stent component responsive to information including at least the parameter relating to the specific patient (e.g. bonder controller 579 supporting an occlusive patch 1322 with a non-occluding expandable wire frame 1321, such as by gluing them at an array of bonding points). In other embodiments a patch, flexible skin, or the like can be buttressed by a wire frame without substantial bonding.

Operation 3327 describes cutting one or more flow holes in a component of the stent responsive to the parameter relating to the specific patient (e.g. laser controller 578, press controller 575, a drill, a punch, or the like cutting a flow hole to form branch outlet 1803 before or after rolling a sheet material into a tube). In some embodiments the flow hole sizes are selected to match stock sizes of sleeves, blood vessel sizes, or the like consistent with the requirements of the stenting site and other medical objectives.

Operation 3328 describes including an antibiotic on the stent responsive to the parameter relating to the specific patient (e.g. applicator controller 564 using antibiotic dispenser 568 for implementing a thickness, surface area, active ingredient concentration, binding agent concentration, drug placement, complementary regimen, or the like to achieve dosage profile 595 selected for the patient). In some embodiments, a flow rate through the intended stent affects a computer model that predicts an antibiotic elution rate for the heuristic stent model.

Referring now to FIG. 34, there are shown several variants of the flow 300 of FIG. 3. Operation 330—receiving a parameter relating to a specific patient—may include one or more of the following operations: 3432 or 3434. Operation 340—customizing one or more junctions of a stent ex situ in response to the received parameter relating to the specific patient—may include one or more of the following operations: 3443, 3444, 3445, 3447, or 3449.

Operation 3432 describes receiving a measurement as the parameter relating to the specific patient (e.g. measurement input 411 receiving a vascular segment length, vascular diameter, vascular wall plaque dimension, vascular calcification level, vascular branch or occlusion location coordinates, or the like). In some embodiments, the measurement can identify a systemic deficiency such as a deficiency of Antithrombin III, Protein C, or Protein S, signaling a hypercoaguability risk. Risks like these can bear toward a more sparing use of stents or a liberal or long-lasting local or systemic regimen of anticoagulants. This can occur, for example, in embodiments in which operation 330 is performed by receiver 430 and in which operation 340 is performed by processing module 580.

Operation 3434 describes receiving a category identifier as the parameter relating to the specific patient (e.g. patient identifier input 413 receiving an indication that a stent is to be provided for a cancer patient, an elderly patient, a patient with an allergy, or the like). Alternatively or additionally, the category identifier can relate to a risk type, a placement site, a stent material, a model name, an emergency status, or the like.

Operation 3443 describes receiving a heuristic model of the one or more junctions of the stent (e.g. network interface 561 receiving stent model 2210, which includes sleeve 2231 joining a conduit between flow port 2201 and flow port 2202). In some embodiments, junctions combine lengths of a stent along a flow path, such as in cases in which a single stent length or width is too large to deploy through a tortuous access. Stent 2300, for example, may be difficult to implant through a femoral artery (not shown) and iliac artery 2235, especially if implemented in a thick material. In one variant, body 2379 is formed and installed initially with openings in lieu of sleeves 2311, 2312, and 2316. Each of the sleeves 2311, 2312, and 2316 can then be placed into its respective opening in turn, the junctions between each sleeve and body 2379 comprising a custom-built friction fit or the like.

Operation 3444 describes updating the heuristic model with the received parameter relating to the specific patient (e.g. model implementer 563 and network interface 561 adjusting stent model 2210 to indicate a "High" tortuosity of an access path through iliac artery 2235). In some embodiments, such an indicator may correspond with a small radius of access vessel curvature, for example, necessitating a looser pleating configuration so that a relatively large and thick stent body material is not deformed inelastically during implantation.

Operation 3445 describes customizing the one or more junctions of the stent with the received heuristic model of the one or more junctions of the stent updated with the received parameter relating to the specific patient (e.g. press controller 575 forming holes in body 2379 via the adjusted stent model 2210 and press 505). The sleeve joints can be adjusted, in this example, so that they are compatible with a design of body 2379 that can survive passage through the tortuous access path.

Operation 3447 describes adapting the one or more junctions of the stent responsive to the received parameter relating to the specific patient (e.g. model implementer 563 and press controller 575 respectively performing operations 3444 and 3445). Alternatively or additionally, operation 3447 can include substance applicator 569 selecting second agent 2615 as a material that can more effectively bind first agent 2618 to sheet material 2612. In some embodiments, machine interface 571 performs operation 3447 by joining junction edges 931, 932 with an adhesive to which the patient is not allergic, responsive to an allergy indication of the patient).

Operation 3449 describes customizing the one or more junctions of the stent as a roughly contemporaneous response to receiving the parameter relating to the specific patient (e.g. sheet bender controller 573 customizing locations of pleats 1651, 1652 with sheet bender 503 so that successive pleats are of irregular spacing, responsive to an indication of a small catheter diameter for the patient). In some embodiments, access vessel diameter and other patient attributes or circumstances dictate a maximum inner diameter of a catheter to be used, for example. Each of the pleats 1651, 1652 in FIG. 16 joins a wider smooth portion to a narrower smooth portion, for example. (This difference facilitates a slight curl of the smooth portions, as shown.) This junction placement configuration permits width differences more than 5% between successive smooth portions, as shown, which facilitates the spiral pleating configuration.

Referring now to FIG. 35, there are shown several variants of the flow 600 of FIG. 6. Operation 610—obtaining a parameter relating to a stent inventory shortage—may include one or more of the following operations: 3513, 3515, or 3518. Operation 620—configuring a stent with a flow occlusion portion in response to the obtained parameter relating to the stent inventory shortage—may include one or more of the following operations: 3521, 3522, 3523, 3527, or 3528.

Operation 3513 describes receiving data at least partly relating to a specific patient including at least the parameter relating to a stent inventory shortage (e.g. inventory status input 419 receiving an indication that no Blue Cross Network healthcare provider currently has a 10% tapering 23 millimeter stent in inventory, responsive to an inquiry identifying the provider and describing the stent type sought). Alternatively or additionally, in some embodiments, the flow occlusion portion of operation 620 is configured in response to the parameter relating to the stent inventory shortage (e.g. shrinking or enlarging flow occlusion portion 922 to adapt an almost-ideal stent responsive to an indication that the ideal stent is currently out of stock). This can occur, for example, in embodiments in which operation 610 is performed by receiver 430 and in which operation 620 is performed by processing module 580.

Operation 3515 describes receiving an indication of a position of an anatomical feature as the parameter relating to the stent inventory shortage (e.g. image input 418 receiving one or more MRI or ultrasound images each with a descriptive annotation indicating that a potential stenting site of a ureter is depicted). In some instances such an annotation can cause model implementer 563 to customize the stent by signaling applicator controller 564 to include an antibiotic, for example.

Operation 3518 describes receiving an indication of an aperture as the parameter relating to the stent inventory shortage (e.g. model input 412 receiving an indication that no stents with secondary apertures larger than 1.1 millimeters in diameter are presently inventoried). In some instances, the received indication may explicitly rank available stents or sheet components in a decreasing order of aperture size match or other suitability indicator. Alternatively or additionally, the ranking may take into account other factors such as an expected custom-stent completion date.

Operation 3521 describes binding an antiproliferative agent to the flow occlusion portion of the stent (e.g. applicator controller 565 binding the agent to at least a portion of an occlusion site at patch 1322 of FIGS. 13-14). This binding can be performed by dipping at least a portion of patch 1322 into antiproliferative agent dispenser 565 (containing rapamycin or cyclosporine, for example) before collapsing stent 1350.

Operation 3522 describes customizing the stent with information relating to a specific patient, the information relating to the specific patient including at least the obtained parameter relating to the stent inventory shortage (e.g. applicator controller 564 or machine interface 571 customizing a coating or structure of a stent component responsive to the specific patient's stenosis risk factors). The flow occlusion site can be widened, or a coating of the site can be made to include a stronger antiproliferative agent, for example, responsive to a high restenosis risk.

Operation 3523 describes allocating the customized stent to the specific patient (e.g. inventory controller 540 modifying stent inventory 542 to indicate that the stent is sold or otherwise reserved for the specific patient relating to specifications used in making that stent). In some embodiments, only a single attribute of the patient can affect a mode of stent customization (e.g. impregnating the stent with an antibiotic responsive to a presence of infection, and otherwise using an off-the-shelf stent). In other embodiments, a combination of patient attributes can affect the mode of stent customization (e.g. selecting a vascular stent size responsive to a combination of indications: size and degree of calcification of a specific vessel, e.g.).

Operation 3527 describes obtaining one or more dimensions of the flow occlusion portion of the stent (e.g. data manager 590 retrieving one or more of a length, width, or thickness of the flow occlusion portion from table 586 responsive to a model identifier of a stent in short supply). In some embodiments, such dimensions can be used for determining a feasibility of constructing an inventory of (a) structurally equivalent flow occlusion stents or (b) functionally-equivalent-but-structurally-distinct flow occlusion stents, closely resembling a stent model approved by the Food and Drug Administration. In some embodiments such determinations can be made automatically, for example in facilitating an efficient mode of compliance with FDA guidelines.

Operation 3528 describes configuring the flow occlusion portion of the stent as the response to the obtained parameter relating to the stent inventory shortage (e.g. model implementer 563 generating a feasible heuristic stent model by adapting the above-referenced approved model to incorporate only components that are available). Machine interface 571 or a remote counterpart thereof can then use the adapted model to configure one or more physical components.

Referring now to FIG. 36, there are shown several variants of the flow 600 of FIG. 6 or 35. Operation 610—obtaining a parameter relating to a stent inventory shortage—may include one or more of the following operations: 3613, 3614, 3616, or 3618. Operation 620—configuring a stent with a flow occlusion portion in response to the obtained parameter relating to the stent inventory shortage—may include one or more of the following operations: 3621, 3622, 3624, 3625, 3626, or 3627.

Operation 3613 describes receiving a stent quantity indicator as the parameter relating to the stent inventory shortage (e.g. inventory status input 419 receiving an indication that a surgeon has asked to reserve one of stent type X and two of stent type Y, and but that only one of each is in stock). In some embodiments an output device indicates a shortage quantity (of the type X, for example) or a proposal for a lot size to be produced.

Operation 3614 describes receiving a material composition indicator as the parameter relating to the stent inventory shortage (e.g. material identifier input 415 indicating that anti-platelent-agent-coated stents are sought from an inventory). In some embodiments model input 412 can combine this with inventory status input 419 to reply that no such stents are available from the inventory, or that only two 14-millimeter-long stents with the specified coating are available.

Operation 3616 describes receiving a shape indicator as the parameter relating to the stent inventory shortage (e.g. message parser 450 receiving an oblong or arc-shaped indicator relating to a surgeon's "ideal stent" model). The shape indicator can be used for generating a "default stent" design that specifies sheet materials, wire materials, medications, coatings, or the like.

Operation 3618 describes receiving a size indicator as the parameter relating to the stent inventory shortage (e.g. dimensional input 416 receiving a diameter, thickness, length, or other feature size relating to an inventoried stent, a readily-made stent, an anatomical feature size for stent customization, or the like). In some embodiments the size indicator is retrieved or requested or accepted via a search tool or a browser, for example.

Operation 3621 describes configuring a wire structure in response to the parameter relating to the stent inventory shortage (e.g. one or more portions of applicator controller 564 forming wire material 2812 into a generally tubular shape). In some embodiments, those skilled in the art can implement operation 3621 by applying teachings herein to adapt construction techniques described in documents like U.S. patent application Ser. No. 10/104,672 ("Modular Stent Graft Assembly and Use Thereof"). Alternatively or additionally, an elastic coating can be used so that deforming the stent will minimize a risk of breakage in the coating. In other embodiments an elastic binding agent is used before or after the primary coating, substantially preventing such breakage. Alternatively or additionally, the primary coating can primarily be applied to portions of sheet material 2612 or wire material 2812 that do not substantially change shape during stent compression or expansion.

Operation 3622 describes constructing the stent with the flow occlusion portion by supporting a flow occlusion structure with the wire structure (e.g. bonder controller 579 assembling the stent with bonder 509 using an occlusive structure customized for identified needs of the specific patient). In some embodiments, press controller 575 can form the structure before the assembly. Alternatively or additionally, network interface 561 can custom-order the occlusive structure.

Operation 3624 describes configuring the flow occlusion portion as a part of the response to the obtained parameter relating to the stent inventory shortage (e.g. substance applicator 569 at least partly coating portion 922 of stent 1000 to implement a patient-specific regimen like that shown in FIG. 27). In some embodiments, those skilled in the art can implement operation 3624 by applying teachings herein to adapt coating techniques described in documents like U.S. patent application Ser. No. 10/915,980 ("Method for Applying Drug Coating to a Medical Device in Surgeon Room").

Operation 3625 describes configuring the stent with the flow occlusion portion as an at-least-roughly contemporaneous response to obtaining the parameter relating to the stent inventory shortage (e.g. substance applicator 569 adding material to a mesh so as to build it up into a flow occlusion portion). In some embodiments substance applicator 569 can essentially pour a viscous biocompatible liquid resin onto the mesh, for example, hardening into a solid occlusion site.

Operation 3626 describes forming a sheet material into a rigid element in response to the obtained parameter relating to the stent inventory shortage (e.g. bonder controller 579 adhesing or otherwise attaching junction edge 931 with junction edge 932 in response to a stent or vessel diameter or circumference consistent with stent profile 1067). In some embodiments, bonder controller 579 controls bonder 509 remotely or with some human assistance. Alternatively or additionally, another portion of machine interface 571 performs a prior operation of cutting sheet material 910 responsive to the obtained parameter.

Operation 3627 describes including at least the rigid element in the stent (e.g. custom processor 560 including at least sheet material 910 in stent 1000). Portions of custom processor 560 can likewise perform additional operations such as coating sheet material 910 as sheet material 2612 (e.g. by portions of applicator controller 564 as described herein and shown in FIG. 26).

Referring now to FIG. 37, there are shown several variants of the flow 600 of FIG. 6, 35, or 36. Operation 610—obtaining a parameter relating to a stent inventory shortage—may include one or more of the following operations: 3711, 3712, 3714, 3716, or 3719. Operation 620—configuring a stent with a flow occlusion portion in response to the obtained parameter relating to the stent inventory shortage—may include one or more of the following operations: 3721, 3722, 3725, 3727, or 3728.

Operation 3711 describes prompting user input (e.g. output device 433 displaying "High" pliability, a "2-3 mm" installed diameter, a "1.5 mm max" collapsed diameter each as default parameter values a user can change via input device 434). In some embodiments, input device 134 includes a pointing device such as can be used to adjust any of these from a pop-up menu of allowable choices. In some embodiments, these or other parameters can be assigned to any value.

Operation 3712 describes receiving the parameter relating to the stent inventory shortage via an interface after prompting the user input (e.g. model input 412 receiving an indication that zero off-the-shelf stents satisfy a sufficiently high percentage of criteria comprising the user input). In some embodiments, model input 412 may then request a custom stent specification using component inventory information such as sheet type input 427, and indicate this specification via output device 433 as the parameter(s) relating to the stent inventory shortage.

Operation 3714 describes receiving an indication of a vascular system structure as the parameter relating to the stent inventory shortage (e.g. vascular type input 422 indicating "true" generally to indicate a vascular device, blood vessel(s) for which the stent(s) are sought, or the like). Categorical information like this can be used for retrieving related models, case histories, available stent and stent component inventories, or the like. It can also be used for deciding upon a customized or off-the-shelf stent, coating, or structural component, for example. In some embodiments, a text-valued vascular type input can likewise be received, such as a blood vessel name.

Operation 3716 describes retrieving the parameter relating to the stent inventory shortage from an inventory (e.g. inventory status input 419 and network interface 435 jointly requesting and receiving a stent or stent component inventory status of all available sources within 100 kilometers of the requester). The identifiers and quantities in the retrieved aggregate stent or stent component inventory can each constitute parameters relating to the stent inventory shortage that can be useful in some instances.

Operation 3719 describes receiving a message comprising at least the parameter relating to the stent inventory shortage (e.g. message parser 450 receiving an advertisement or other source indication that can provide a wire type input such as a wire gauge or wire alloy description). In some embodiments, message parser 450 may be implemented as a web crawler that independently gathers stent information from diverse suppliers or specifications.

Operation 3721 describes configuring the stent with a pleat configuration responsive to the obtained parameter relating to the stent inventory shortage (e.g. sheet bender controller 573 forming helical or other substantially curvaceous pleats with sheet bender 503). See, for example, pleats 1652 of FIG. 16. In some embodiments, a collapse-pleating configuration can be computer-optimized to minimize a risk of buckling or other damage as a custom-pleated stent passes through a real catheter mimicked by a heuristic catheter model. For example, in some instances a catheter can be modeled adequately by an inner diameter (such as diameter 1667 of FIG. 16) and a degree of tortuosity (such as H, M, or L). In some embodiments the collapse-pleating configuration can likewise take into account an inner diameter of a collapsed stent (such as diameter 1668 of FIG. 16) or other factors as described herein.

Operation 3722 describes including the flow occlusion portion of the stent responsive to the obtained parameter relating to the stent inventory shortage (e.g. stock designator 562 and sheet inventory 541 jointly nominating sheet material 910 having flow occlusion portion 922 responsive to indications that sheet material 910 is the only on-site component of a desired rigidity and that flow occlusion portion 922 will not impair stent performance). Of course in other embodiments, as explained above, a flow occlusion portion may be a value-enhancing stent feature, a required search criterion, or a significant feature presented to a system user to facilitate the system user's stent selection. Also in other instances the flow occlusion portion is included by machine interface 571 configuring the stent physically with such a feature.

Operation 3725 describes configuring the stent with a dividing flow path responsive to the obtained parameter relating to the stent inventory shortage (e.g. machine interface 571 automatically configuring stent 1800 with flow outlet 1802 and at least branch outlet 1803, responsive to an indication that no suitable branching stents are available in inventory). In some embodiments, operation 3725 is initially performed virtually, yielding an image like FIG. 18 as a heuristic model. A large number of such models can be kept as a virtual "inventory," in some implementations, optionally including linkages to component availability information that can bear upon a delivery time estimate.

Operation 3727 describes configuring the stent with the flow occlusion portion in response to a pathological indication and to the obtained parameter relating to the stent inventory shortage (e.g. plant 570 causing press controller 575 to create a flow occlusion site more than 90% blocked, responsive to an indication of an arterial rupture). Alternatively or additionally, the flow occlusion portion can be implemented as a thrombogenic surface positioned in a thrombogenic target zone such as that shown in FIGS. 18 & 19.

Operation 3728 describes applying information retrieved relating to the stent with the flow occlusion portion (e.g. sheet bender controller 573 implementing one or more pleats in sheet material 910 or in stent 1000 responsive to information about flow occlusion portion 922). In some instances, pleats may be denser in a remainder (e.g. mesh portion 921) of a sheet component, or may be omitted entirely from a flow occlusion portion to minimize inelastic deformation.

Referring now to FIG. 38, there are shown several variants of the flow 700 of FIG. 7. Operation 760—receiving a parameter relating to a specific patient—may include one or more of the following operations: 3863 or 3869. Operation 770—configuring a stent with a flow occlusion portion in response to receiving the parameter relating to the specific patient—may include one or more of the following operations: 3871, 3873, 3875, 3876, or 3878.

Operation 3863 describes obtaining an identifier of the specific patient as the parameter relating to the specific patient (e.g. patient identifier input 413 requesting the patient's identification number responsive to name fragments received, such as from an intake nurse). Alternatively or additionally, complete or local records for the patient can be retrieved directly in response to the name fragments or other patient identifier initially received. This approach can accelerate a stent customization, for example, especially in or near an emergency care facility. This can occur, for example, in embodiments in which operation 760 is performed by receiver 430 and in which operation 770 is performed by processing module 580.

Operation 3869 describes obtaining medical history information including at least the parameter relating to the specific patient (e.g. message parser 450 assembling the patient's history as portions thereof arrive, and extracting at least a reasonably current vessel diameter as the parameter). In some embodiments, model input 412 instead generates stent diameter or thickness as the parameter (from the vessel diameter, e.g.).

Operation 3871 describes forming the flow occlusion portion of the stent by supporting a substantially occlusive layer with a rigid flow-permeable mesh (e.g. bonder controller 579 affixing patch 1322 to frame 1321 with bonder 509). For variants incorporating features like operation 3871, a layer can be substantially occlusive if it occludes at least about 80% of a defined channel cross section. In some embodiments, a first and second stent portion are designed to be assembled in situ, such as by installing a film, a somewhat flimsy stent, or the like and then supporting it in situ against a vessel wall with a rigid frame. See FIG. 16. In some embodiments, those skilled in the art can implement operation 3871 by applying teachings herein to adapt assembly techniques described in documents like U.S. patent application Ser. No. 10/737,314 ("Assembly and Planar Structure for Use Therein Which is Expandable into a 3-D Structure Such as a Stent and Device for Making the Planar Structure").

Operation 3873 describes heat-treating at least a portion of the one or more stents responsive to the parameter relating to the stent inventory shortage (e.g. machine interface 571 shaping nitinol or other superelastic material at 400° to 500° Celsius using a heuristic model that includes a temperature or other measurable parameter). In some embodiments, the parameter can be a thickness or other model dimension or a treatment temperature. In some embodiments, those skilled in the art can implement operation 3873 by applying teachings herein to adapt construction techniques described in documents like U.S. patent application Ser. No. 10/826,028 ("Sizing and Shaping Device for Treating Congestive Heart Failure").

Operation 3875 describes removing material from the stent in the response to receiving the parameter relating to the specific patient (e.g. model implementer 563 forming notches, perforations, or the like responsive to an indication that a heuristic stent or component model needs a higher flexibility or coating elution rate). Operation 3875 can also be performed physically, such as by a chemical etch (or by laser controller 578 or the like) forming or enlarging holes 925 of FIG. 9. In some embodiments, mesh portion 921 can be made more flexible and flow-permeable as the diameters of holes 925 are increased slightly, responsive to a shortage, patient attribute, or the like.

Operation 3876 describes configuring the stent with a flow-permeable mesh in the response to receiving the parameter relating to the specific patient (e.g. machine interface 571 positioning a diffuse emboli-deflecting mesh responsive to an indication that the permeating flow will supply a carotid artery or other location vulnerable to emboli). In some embodiments, a diffuse emboli-deflecting mesh is one with about 50 to 5000 flow holes per square centimeter and an effective areal coverage of at most about 20%.

Operation 3878 describes configuring the flow occlusion portion of the stent in the response to receiving the parameter relating to the specific patient (e.g. substance applicator 569 or machine interface 571 configuring thrombogenic surface 1863 of FIG. 18). In some embodiments, a thrombogenic surface can be a cellulose-based compound, a bare metal, or otherwise at least about as thrombogenic as pure titanium.

Referring now to FIG. 39, there are shown several variants of the flow 800 of FIG. 8. Operation 880—obtaining a parameter relating to a stent inventory shortage—may include one or more of the following operations: 3984 or 3986. Operation 890—specializing one or more stents in response to obtaining the parameter relating to the stent inventory shortage configuring a stent with a flow occlusion portion in response to the obtained parameter relating to the stent inventory shortage—may include one or more of the following operations: 3992, 3993, 3995, 3996, or 3998.

Operation 3984 describes obtaining anatomical information including at least the parameter relating to the stent inventory shortage (e.g. inventory controller 540 accessing stent inventory 542 to determine that it includes no stents of suitable size and rigidity for effectively stenting a trachea, esophagus, or the like). In some embodiments, such a determination is made responsive to arithmetic combinations, quantitative comparisons or the like, substantially in lieu of specific anatomical name comparisons. This can occur, for example, in embodiments in which operation 880 is performed by receiver 430 and in which operation 890 is performed by processing module 580.

Operation 3986 describes obtaining stent information including at least the parameter relating to the stent inventory shortage (e.g. wire type input 426 receiving an indication that a wire component of a heuristic stent model has a category of "custom" or other indication that the wire is not generic). In some embodiments, such an indication signifies that such wire is never in inventory and must be special ordered or replaced with some other design structure.

Operation 3992 describes exerting pressure on a component of the one or more stents responsive to the parameter relating to the stent inventory shortage (e.g. sheet bender controller 573 forming pleats 1415 with sheet bender 503 in a configuration substantially like that of a stent in short supply). In some embodiments, the component is assembled into the stent(s) after operation 3992.

Operation 3993 describes specializing the one or more stents responsive to a value of a parameter relating to a specific patient (e.g. network interface 561 causing stent 2150 to implement radius of curvature 2152 for duct 2024 of patient 2000). In some embodiments, network interface 561 configures stent 2150 via a manufacturing or customization facility (not shown) that can be remote from patient 2000 or system 500.

Operation 3995 describes removing a portion of the one or more stents responsive to the parameter relating to the stent inventory shortage (e.g. laser controller 578 scoring, notching, or otherwise removing material with laser 508 along a pleat defined in a novel stent pleating configuration identified by the parameter). Alternatively or additionally, the removed portion may include a stent length portion removed by cutting (via machine interface 571, e.g.) responsive to a length indicator. Alternatively or additionally, the removed portion may include a stent thickness removed by chemical etching (via applicator controller 564, e.g.) responsive to a thickness indicator. Alternatively or additionally any portion of a virtual stent can be removed by model implementer 563, in some embodiments, responsive to a similar stent being depleted or otherwise in short supply.

Operation 3996 describes including an antibiotic in the one or more stents (e.g. antibiotic dispenser 568 applying a rapamycin-containing mixture locally in response to the parameter indicating that no better antibiotic is apparently available commercially). In some embodiments, a message describing this information can instead be provided to a doctor who can then authorize or implement the rapamycin-including mixture coating operation.

Operation 3998 describes forming an aperture in the one or more stents responsive to the parameter relating to the stent inventory shortage (e.g. machine interface 571 forming an opening responsive to flow port 2202 of stent model 2210, responsive to an indication that flow port 2202 is substantially unlike that of any stent in inventory). In some embodiments, such an indication can come from an interface such as by input device 434, a mouse or other pointing device, or the like.

It will be understood that variations in business models relating to the technologies described herein may prove advantageous, for example in situations in which an information systems consultant or other service provider acts for the benefit of one or more clients or interests to achieve such technologies collectively. Such arrangements can facilitate organizational or tool specialization and cost effectiveness, for example, across distributed networks in the global marketplace. Those skilled in the art will recognize that such beneficial interaction creates a commercial web constituting a single de facto entity of two or more interacting participants cooperatively implementing the teachings herein, within the scope and spirit of the claimed invention.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
   means for accessing at least one of an inventory, an advertisement, or other source indication of available stents;
   means for automatically obtaining data output of one or more parameters of one or more medical devices that reveal a stent inventory shortage, the means for automatically obtaining data output utilizing direct availability information or one or more indirect indications designating an order as an emergency status or other parameter indicating an elevated priority; and
   means for configuring one or more stents with a flow occlusion portion in response to the one or more automatically obtained parameters indicating the existence of the stent inventory shortage, the one or more stents including at least one of a structurally equivalent flow occlusion stent, or a functionally-equivalent-but-structurally-distinct flow occlusion stent resembling a stent model approved by a regulation administration.

2. The system of claim 1 in which the means for automatically obtaining data output of one or more parameters of one or more medical devices that reveal a stent inventory shortage comprises:
   means for receiving data at least partly relating to a specific patient including at least the one or more parameters that reveal a stent inventory shortage.

3. The system of claim 1 in which the means for automatically obtaining data output of one or more parameters of one or more medical devices that reveal a stent inventory shortage comprises:
   means for receiving an indication of a position of an anatomical feature as the one or more parameters that reveal the stent inventory shortage.

4. The system of claim 1 in which the means for configuring one or more stents with a flow occlusion portion in response to the one or more automatically obtained parameters indicating the existence of the stent inventory shortage comprises:
   means for binding an antiproliferative agent to the flow occlusion portion of the one or more stents.

5. The system of claim 1 in which the means for configuring one or more stents with a flow occlusion portion in response to the one or more automatically obtained parameters indicating the existence of the stent inventory shortage comprises:
   means for customizing the one or more stents with information relating to a specific patient, the information relating to the specific patient including at least the one or more automatically obtained parameters that reveal the stent inventory shortage; and
   means for allocating the one or more customized stents to the specific patient.

6. The system of claim 1 in which the means for configuring one or more stents with a flow occlusion portion in response to the one or more automatically obtained parameters indicating the existence of the stent inventory shortage comprises:
   means for configuring a wire structure in response to the one or more parameters that reveal the stent inventory shortage; and
   means for constructing the one or more stents with the flow occlusion portion by supporting a flow occlusion structure with the wire structure.

7. The system of claim 1 in which the means for configuring one or more stents with a flow occlusion portion in response to the one or more automatically obtained parameters indicating the existence of the stent inventory shortage comprises:
   means for configuring the flow occlusion portion as a part of the response to the one or more automatically obtained parameters that reveal the stent inventory shortage.

8. The system of claim 1 in which the means for configuring one or more stents with a flow occlusion portion in response to the one or more automatically obtained parameters indicating the existence of the stent inventory shortage comprises:
   means for configuring the one or more stents with the flow occlusion portion as an at-least-roughly contemporaneous response to automatically obtaining the one or more parameters that reveal the stent inventory shortage.

9. The system of claim 1 in which the means for configuring one or more stents with a flow occlusion portion in response to the one or more automatically obtained parameters indicating the existence of the stent inventory shortage comprises:

means for forming a sheet material into a rigid element in response to the one or more automatically obtained parameters that reveal the stent inventory shortage; and means for including at least the rigid element in the one or more stents.

10. The system of claim 1 in which the means for automatically obtaining data output of one or more parameters of one or more medical devices that reveal a stent inventory shortage comprises:

means for prompting user input; and means for receiving the one or more parameters that reveal the stent inventory shortage via an interface after prompting the user input.

11. The system of claim 1 in which the means for configuring one or more stents with a flow occlusion portion in response to the one or more automatically obtained parameters indicating the existence of the stent inventory shortage comprises:

means for configuring the one or more stents with a pleat configuration responsive to the one or more automatically obtained parameters that reveal the stent inventory shortage.

12. The system of claim 1 in which the means for configuring one or more stents with a flow occlusion portion in response to the one or more automatically obtained parameters indicating the existence of the stent inventory shortage comprises:

means for including the flow occlusion portion of the one or more stents responsive to the one or more automatically obtained parameters that reveal the stent inventory shortage.

13. The system of claim 1 in which the means for configuring one or more stents with a flow occlusion portion in response to the one or more automatically obtained parameters indicating the existence of the stent inventory shortage comprises:

means for configuring the one or more stents with a dividing flow path responsive to the one or more automatically obtained parameters that reveal the stent inventory shortage.

14. The system of claim 1 in which the means for configuring one or more stents with a flow occlusion portion in response to the one or more automatically obtained parameters indicating the existence of the stent inventory shortage comprises:

means for configuring the one or more stents with the flow occlusion portion in response to a pathological indication and to the one or more automatically obtained parameters that reveal the stent inventory shortage.

15. A system comprising:

circuitry for accessing at least one of an inventory, an advertisement, or other source indication of available stents;

circuitry for automatically obtaining data output of one or more parameters of one or more medical devices that reveal a stent inventory shortage, the circuitry for automatically obtaining data output utilizing direct availability information or one or more indirect indications designating an order as an emergency status or other parameter indicating an elevated priority; and circuitry for configuring one or more stents with a flow occlusion portion in response to the one or more automatically obtained parameters indicating the existence of the stent inventory shortage, the one or more stents including at least one of a structurally equivalent flow occlusion stent, or a functionally-equivalent-but-structurally-distinct flow occlusion stent resembling a stent model approved by a regulation administration.

16. The system of claim 15 in which the circuitry for automatically obtaining data output of one or more parameters of one or more medical devices that reveal a stent inventory shortage comprises:

circuitry for receiving data at least partly relating to a specific patient including at least the one or more parameters that reveal a stent inventory shortage.

17. The system of claim 15 in which the circuitry for automatically obtaining data output of one or more parameters of one or more medical devices that reveal a stent inventory shortage comprises:

circuitry for receiving an indication of a position of an anatomical feature as the one or more parameters that reveal the stent inventory shortage.

18. The system of claim 15 in which the circuitry for automatically obtaining data output of one or more parameters of one or more medical devices that reveal a stent inventory shortage comprises:

circuitry for receiving an indication of an aperture as the one or more parameters that reveal the stent inventory shortage.

19. The system of claim 15, further comprising:

an applicator controller; and circuitry for customizing the one or more stents via the applicator controller and with information relating to a specific patient, the information relating to the specific patient including at least the one or more automatically obtained parameters that reveal the stent inventory shortage.

20. The system of claim 15 in which the circuitry for automatically obtaining data output of one or more parameters of one or more medical devices that reveal a stent inventory shortage comprises:

circuitry for receiving a stent quantity indicator as the one or more parameters that reveal the stent inventory shortage.

21. The system of claim 15 in which the circuitry for automatically obtaining data output of one or more parameters of one or more medical devices that reveal a stent inventory shortage comprises:

circuitry for receiving a material composition indicator as the one or more parameters that reveal the stent inventory shortage.

22. The system of claim 15 in which the circuitry for automatically obtaining data output of one or more parameters of one or more medical devices that reveal a stent inventory shortage comprises:

circuitry for receiving a shape indicator as the one or more parameters that reveal the stent inventory shortage.

23. The system of claim 15 in which the circuitry for automatically obtaining data output of one or more parameters of one or medical devices that reveal a stent inventory shortage comprises:

circuitry for receiving a size indicator as the one or more parameters that reveal the stent inventory shortage.

24. The system of claim 15 in which the circuitry for configuring one or more stents with a flow occlusion portion in response to the one or more automatically obtained parameters indicating the existence of the stent inventory shortage comprises:

circuitry for configuring the one or more stents with the flow occlusion portion as an at-least-roughly contemporaneous response to automatically obtaining the one or more parameters that reveal the stent inventory shortage.

25. The system of claim 15 in which the circuitry for automatically obtaining data output of one or more parameters of one or more medical devices that reveal a stent inventory shortage comprises:
 circuitry for prompting user input; and
 circuitry for receiving the one or more parameters that reveal the stent inventory shortage via an interface after prompting the user input.

26. The system of claim 15 in which the circuitry for automatically obtaining data output of one or more parameters of one or more medical devices that reveal a stent inventory shortage comprises:
 circuitry for receiving an indication of a vascular system structure as the one or more parameters that reveal the stent inventory shortage.

27. The system of claim 15 in which the circuitry for automatically obtaining data output of one or more parameters of one or more medical devices that reveal a stent inventory shortage comprises:
 circuitry for retrieving the one or more parameters that reveal the stent inventory shortage from an inventory.

28. The system of claim 15 in which the circuitry for automatically obtaining data output of one or more parameters of one or more medical devices that reveal a stent inventory shortage comprises:
 circuitry for receiving a message comprising at least the one or more parameters that reveal the stent inventory shortage.

29. The system of claim 15, further comprising:
 a sheet bender; and
 circuitry for configuring the one or more stents with a pleat configuration via the sheet bender and responsive to the one or more automatically obtained parameters that reveal the stent inventory shortage.

30. The system of claim 15 in which the circuitry for configuring one or more stents with a flow occlusion portion in response to the one or more automatically obtained parameters indicating the existence of the stent inventory shortage comprises:
 circuitry for configuring the stent with the flow occlusion portion in response to a pathological indication and to the one or more automatically obtained parameters that reveal the stent inventory shortage.

31. The system of claim 15 in which the circuitry for configuring one or more stents with a flow occlusion portion in response to the one or more automatically obtained parameters indicating the existence of the stent inventory shortage comprises:
 circuitry for applying information retrieved relating to the one or more stents with the flow occlusion portion.

32. The system of claim 15, further comprising:
 a local user interface output device operably coupled to the circuitry for automatically obtaining the one or more parameters that reveal the stent inventory shortage.

33. The system of claim 15, further comprising:
 a network interface operably coupled to the circuitry for configuring one or more stents with a flow occlusion portion in response to the one or more automatically obtained parameters indicating the existence of the stent inventory shortage.

34. The system of claim 15, further comprising:
 an antibiotic dispenser operably coupled to the circuitry for configuring one or more stents with a flow occlusion portion in response to the one or more automatically obtained parameters indicating the existence of the stent inventory shortage.

35. The system of claim 15, further comprising:
 a stock designator operably coupled to the circuitry for configuring one or more stents with a flow occlusion portion in response to the one or more automatically obtained parameters indicating the existence of the stent inventory shortage.

36. The system of claim 15, further comprising:
 a substance applicator operably coupled to the circuitry for configuring one or more stents with a flow occlusion portion in response to the one or more automatically obtained parameters indicating the existence of the stent inventory shortage.

37. The system of claim 15, further comprising:
 a machine interface operably coupled to the circuitry for configuring one or more stents with a flow occlusion portion in response to the one or more automatically obtained parameters indicating the existence of the stent inventory shortage.

38. The system of claim 15, further comprising:
 a scribe operably coupled to the circuitry for configuring one or more stents with a flow occlusion portion in response to the one or more automatically obtained parameters indicating the existence of the stent inventory shortage.

39. The system of claim 15, further comprising:
 a sheet bender operably coupled to the circuitry for configuring one or more stents with a flow occlusion portion in response to the one or more automatically obtained parameters indicating the existence of the stent inventory shortage.

40. The system of claim 15, further comprising:
 a press operably coupled to the circuitry for configuring one or more stents with a flow occlusion portion in response to the one or more automatically obtained parameters indicating the existence of the stent inventory shortage.

41. The system of claim 15, further comprising:
 a laser operably coupled to the circuitry for configuring one or more stents with a flow occlusion portion in response to the one or more automatically obtained parameters indicating the existence of the stent inventory shortage.

42. The system of claim 15, further comprising:
 a bonder operably coupled to the circuitry for configuring one or more stents with a flow occlusion portion in response to the one or more automatically obtained parameters indicating the existence of the stent inventory shortage.

43. The system of claim 15, further comprising:
 a data aggregator operably coupled to the circuitry for configuring one or more stents with a flow occlusion portion in response to the one or more automatically obtained parameters indicating the existence of the stent inventory shortage.

44. The system of claim 1, wherein the means for automatically obtaining data output of one or more parameters of one or more medical devices that reveal a stent inventory shortage comprises:
 means for automatically obtaining data output of one or more sensor and/or imaging medical devices one or more parameters that reveal a stent inventory shortage.

45. The system of claim 1, wherein the means for automatically obtaining data output of one or more parameters of one or more medical devices that reveal a stent inventory shortage comprises:

means for automatically obtaining an access path and/or a tortuosity data output of one or more medical devices one or more parameters that reveal a stent inventory shortage.

46. The system of claim 1, wherein the means for configuring one or more stents with a flow occlusion portion in response to the one or more automatically obtained parameters indicating the existence of the stent inventory shortage comprises:

means for configuring upon authorization confirmation one or more stents with a flow occlusion portion in response to the one or more automatically obtained parameters indicating the existence of the stent inventory shortage.

47. The system of claim 1, wherein the means for configuring one or more stents with a flow occlusion portion in response to the one or more automatically obtained parameters indicating the existence of the stent inventory shortage comprises:

means for configuring one or more stents with a flow occlusion portion in response to the one or more automatically obtained parameters indicating the existence of the stent inventory shortage and without requiring contemporaneous participation by a healthcare provider.

48. The system of claim 1, further comprising:
means for customizing a medication regimen based at least in part upon the one or more stents.

* * * * *